United States Patent
Pohlman et al.

(10) Patent No.: US 8,017,554 B2
(45) Date of Patent: Sep. 13, 2011

(54) 3-AMINO-1,2-BENZISOTHIAZOLE COMPOUNDS FOR COMBATING ANIMAL PEST

(75) Inventors: Matthias Pohlman, Freinsheim (DE); Wolfgang von Deyn, Neustadt (DE); Florian Kaiser, Mannheim (DE); Ernst Baumann, Dudenhofen (DE); Michael Rack, Eppelheim (DE); Douglas D. Anspaugh, Apex, NC (US); Deborah L. Culbertson, Fuquay Varina, NC (US); Henry Van Tuyl Cotter, Raleigh, NC (US)

(73) Assignee: BASF SE, Ludwigshafen (DE)

( * ) Notice: Subject to any disclaimer, the term of this patent is extended or adjusted under 35 U.S.C. 154(b) by 249 days.

(21) Appl. No.: 12/294,753

(22) PCT Filed: Mar. 22, 2007

(86) PCT No.: PCT/EP2007/052738
§ 371 (c)(1),
(2), (4) Date: Sep. 26, 2008

(87) PCT Pub. No.: WO2007/113119
PCT Pub. Date: Oct. 11, 2007

(65) Prior Publication Data
US 2010/0167922 A1    Jul. 1, 2010

Related U.S. Application Data

(60) Provisional application No. 60/787,809, filed on Mar. 31, 2006.

(51) Int. Cl.
*A01C 1/06* (2006.01)
*A01N 43/80* (2006.01)
*C07D 275/04* (2006.01)

(52) U.S. Cl. .................. 504/100; 504/269; 548/212
(58) Field of Classification Search .................. 504/100; 548/212; 514/373
See application file for complete search history.

(56) References Cited

U.S. PATENT DOCUMENTS

| | | | |
|---|---|---|---|
| 3,600,154 A | 8/1971 | Slot et al. | |
| 3,707,364 A | 12/1972 | Becke et al. | |
| 4,492,705 A | 1/1985 | Drabek | |
| 4,698,358 A | 10/1987 | Drabek | |
| 4,760,076 A | 7/1988 | Drabek | |
| 4,786,650 A | 11/1988 | Drabek | |
| 5,981,758 A | 11/1999 | Plath et al. | |
| 2007/0071782 A1 | 3/2007 | Deyn et al. | |
| 2010/0009848 A1 | 1/2010 | von Deyn et al. | |

FOREIGN PATENT DOCUMENTS

| | | |
|---|---|---|
| DE | 1 545 842 | 12/1969 |
| DE | 1 915 387 | 10/1970 |
| DE | 1 670 920 | 4/1971 |
| DE | 1 667 970 | 7/1971 |
| DE | 3 544 436 | 6/1986 |
| DE | 3 607 343 | 9/1986 |
| EP | 0 033 984 | 8/1981 |
| EP | 0 086 748 | 8/1983 |
| EP | 0 110 829 | 6/1984 |
| EP | 0 133 418 | 2/1985 |
| EP | 0 138 762 | 4/1985 |
| EP | 0 191 734 | 8/1986 |
| EP | 0 207 891 | 1/1987 |
| EP | 0 945 449 | 9/1999 |
| JP | 1 319467 | 12/1989 |
| JP | 6 220030 | 8/1994 |
| WO | WO 03/087072 | 10/2003 |
| WO | WO 2005/035486 | 4/2005 |
| WO | WO 2006/091858 | 8/2006 |
| WO | WO 2007/030582 | 3/2007 |
| WO | WO 2007/057407 | 5/2007 |

OTHER PUBLICATIONS

International Search Report, completed Jul. 16, 2007, in corresponding International Application No. PCT/EP2007/052738, filed Mar. 22, 2007.
International Preliminary Report on Patentability completed Apr. 30, 2008, in corresponding International Application No. PCT/EP2007/052738, filed Mar. 22, 2007.

*Primary Examiner* — Golam M M Shameem
*Assistant Examiner* — Kristin Bianchi
(74) *Attorney, Agent, or Firm* — Brinks Hofer Gilson & Lione

(57) ABSTRACT

The present invention relates to 3-amino-1,2-benzisothiazole compounds of formula I

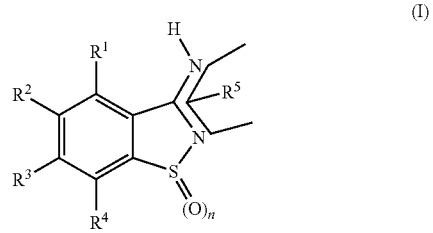

(I)

wherein $R^1$, $R^2$, $R^3$, $R^4$, $R^5$ and n are defined in the description.
The present invention relates to insecticidal compounds of formula I and to their isomeric imino derivatives, as well as to the enantiomers, diastereomers and salts thereof and to compositions comprising such compounds. The invention also relates to the use of the 3-amino-1,2-benzisothiazole compounds, of their salts or of compositions comprising them for combating animal pests. Furthermore the invention relates also to methods of applying such compounds.

20 Claims, No Drawings

3-AMINO-1,2-BENZISOTHIAZOLE COMPOUNDS FOR COMBATING ANIMAL PEST

This application is a National Stage application of International Application No. PCT/EP2007/052738 filed Mar. 22, 2007, which claims the benefit of U.S. Provisional Application No. 60/787,809 filed Mar. 31, 2006, the entire contents of which is hereby incorporated herein by reference.

The present invention relates to 3-amino-1,2-benzisothiazole compounds and to their isomeric imino derivatives, as well as to the enantiomers, diastereomers and salts thereof and to compositions comprising such compounds. The invention also relates to the use of the 3-amino-1,2-benzisothiazole compounds, of their salts or of compositions comprising them for combating animal pests. Furthermore the invention relates also to methods of applying such compounds.

Animal pests destroy growing and harvested crops and attack wooden dwelling and commercial structures, causing large economic loss to the food supply and to property. While a large number of pesticidal agents are known, due to the ability of target pests to develop resistance to said agents, there is an ongoing need for new agents for combating animal pests. In particular, animal pests such as insects and acaridae are difficult to be effectively controlled.

It is therefore an object of the present invention to provide compounds having a good pesticidal activity, especially against difficult to control insects and acaridae.

It has been found that these objects are solved by 3-amino-1,2-benzisothiazole derivatives of the general formula I:

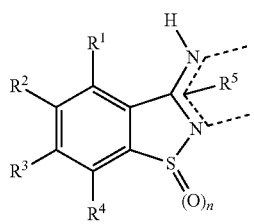

(I)

wherein n is 0, 1 or 2;

$R^1$ is selected from $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, wherein the mentioned radicals may be unsubstituted or may carry 1, 2 or 3 radicals, selected from the group consisting of cyano, nitro, amino, $C_1$-$C_4$-alkoxy, $C_1$-$C_4$-alkylthio, $C_1$-$C_4$-alkylsulfinyl, $C_1$-$C_4$-alkylsulfonyl, $C_1$-$C_4$-haloalkoxy, $C_1$-$C_4$-haloalkylthio, ($C_1$-$C_4$-alkoxy)carbonyl, ($C_1$-$C_4$-alkyl)amino, di($C_1$-$C_4$-alkyl)amino, aminocarbonyl, ($C_1$-$C_4$-alkyl)aminocarbonyl, di($C_1$-$C_4$-alkyl)aminocarbonyl, $C_3$-$C_8$-cycloalkyl and phenyl, it being possible for phenyl to be unsubstituted, partially or fully halogenated and/or to carry 1, 2 or 3 substituents, independently of one another selected from the group consisting of CN, $C_1$-$C_4$-alkyl, $C_1$-$C_4$-haloalkyl, $C_1$-$C_4$-alkoxy and $C_1$-$C_4$-haloalkoxy and $R^2$, $R^3$ and $R^4$ are independently of one another selected from the group consisting of hydrogen, halogen, cyano, azido, nitro, $C_1$-$C_6$-alkyl, $C_3$-$C_8$-cycloalkyl, $C_1$-$C_4$-haloalkyl, $C_1$-$C_4$-alkoxy, $C_1$-$C_4$-alkylthio, $C_1$-$C_4$-alkylsulfonyl, $C_1$-$C_4$-haloalkoxy, $C_1$-$C_4$-haloalkylthio, $C_2$-$C_6$-alkenyl, $C_2$-$C_6$-alkynyl, ($C_1$-$C_4$-alkoxy)carbonyl, amino, ($C_1$-$C_4$-alkyl)amino, di($C_1$-$C_4$-alkyl)amino, aminocarbonyl, ($C_1$-$C_4$-alkyl)aminocarbonyl, di($C_1$-$C_4$-alkyl)aminocarbonyl, sulfonyl, sulfonylamino, sulfenylamino, sulfanylamino and C(=O)—$R^{2a}$ or C(=O)—$R^{3a}$ or C(=O)—$R^{4a}$, and wherein, $R^{2a}$ or $R^{3a}$ or $R^{4a}$ are selected from the group consisting of hydrogen, hydroxy, $C_1$-$C_5$-alkoxy, amino, $C_1$-$C_6$-alkyl, aryl, aryl-$C_1$-$C_6$-alkyl, ($C_1$-$C_6$-alkyl)-amino, di-($C_1$-$C_6$-alkyl)-amino, 3- to 7-membered heteroaryl or heteroaryl-$C_1$-$C_4$-alkyl, wherein the heteroaryl ring contains as ring members 1, 2 or 3 heteroatoms, selected from the group consisting of nitrogen, oxygen, sulfur, a group SO, $SO_2$ or $NR^{2b}$ or $NR^{3b}$ or $NR^{4b}$, and wherein $R^{2b}$ or $R^{3b}$ or $R^{4b}$ are hydrogen, $C_1$-$C_6$-alkyl or ($C_1$-$C_6$-alkyl)-carbonyl;

$R^5$ is selected from the group consisting of hydrogen, $OR^{5a}$, $C_1$-$C_{10}$-alkyl, $C_2$-$C_{10}$-alkenyl, $C_2$-$C_{10}$-alkinyl, $C_3$-$C_{10}$-cycloalkyl, hetaryl-$C_1$-$C_4$-alkyl, heterocyclyl-$C_1$-$C_4$-alkyl, wherein these radicals may be unsubstituted, partially or fully halogenated and/or may carry 1-4 radicals selected from the group consisting of $C_1$-$C_{10}$-alkoxy, $C_1$-$C_{10}$-alkylthio, $C_1$-$C_{10}$-alkylsulfinyl, $C_1$-$C_{10}$-alkylsulfonyl, $C_1$-$C_{10}$-haloalkoxy, $C_1$-$C_{10}$-haloalkylthio, ($C_1$-$C_{10}$-alkoxy)carbonyl, cyano, nitro, amino, ($C_1$-$C_{10}$-alkyl)amino, di-($C_1$-$C_{10}$-alkyl)amino, $C_3$-$C_{10}$-cycloalkyl and phenyl, it being possible for phenyl to be unsubstituted, partially or fully halogenated and/or to carry 1-3 substituents selected from the group consisting of CN, $C_1$-$C_6$-alkyl, $C_1$-$C_6$-haloalkyl, $C_1$-$C_6$-alkoxy, $C_1$-$C_6$-haloalkoxy, and wherein $R^{5a}$ is selected from hydrogen, $C_1$-$C_{10}$-alkyl, $C_1$-$C_{10}$-acyl, $C_3$-$C_{10}$-cycloalkyl, $C_2$-$C_{10}$-alkenyl, $C_2$-$C_{10}$-alkynyl, aryl, aryl-$C_1$-$C_4$-alkyl, heteroaryl and heteroaryl-$C_1$-$C_4$-alkyl, heterocyclyl or heterocyclyl-$C_1$-$C_4$-alkyl and wherein all radicals may be unsubstituted, partially or fully halogenated and/or may carry 1, 2 or 3 radicals, selected from the group consisting of cyano, nitro, amino, $C_1$-$C_4$-alkoxy, $C_1$-$C_4$-alkylthio, $C_1$-$C_4$-alkylsulfinyl, $C_1$-$C_4$-alkylsulfonyl, $C_1$-$C_4$-haloalkoxy, $C_1$-$C_4$-haloalkylthio, ($C_1$-$C_4$-alkoxy)carbonyl, ($C_1$-$C_4$-alkyl)amino, di($C_1$-$C_4$-alkyl)amino and $C_3$-$C_8$-cycloalkyl;

or the enantiomers, distereomers or salts thereof, with the proviso that if n is 0, $R^5$ is not hydrogen.

Formula I can also be represented by the following two isomeric formulae

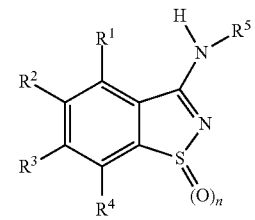

Formula Ia

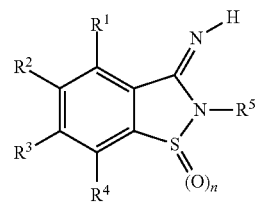

Formula Ib

Depending on the substitution pattern, the compounds of formula I can contain one or more chiral centers, in which case they are present as enantiomer or diastereomer mixtures. Subject matter of this invention are not only compositions containing these mixtures but also those containing the pure enantiomers or diastereomers.

Some compounds of formula I have been described inter alia in DE-A 1915387, WO 03/87072, JP-A 06220030, DE-A 1670920 and DE-A 1545842. However, an insecticidal, acaricidal or nematicidal activity of compounds of formula I have not been disclosed yet.

Amino- and amino-acylated 1,2-benzisothiazole compounds have been described by Drabek for an insecticidal activity in EP-A 207891, EP-A 191734, DE-A 3544436, EP-A 138762, EP-A 133418 and EP-A 110829, or 3-Amidinobenzisothiazole 1,1-dioxides for same use in EP-A 86748. JP-A 01319467 describes the preparation of N-acylated amino-benzisothiazoles and their 1,2-dioxyde derivatives as active ingredients for insecticidal purposes. Sulfonyl compounds and aphicidal compositions based on mono-substituted 3-amino-1,2-benzisothiazole-1,1-dioxyde derivatives have been described in EP-A 0033984. The latter EP-A 33984 discloses 2-cyanobenzene sulfonamides having aphicidal activity. Their activity, however, is not satisfactory. Similar compounds to EP-A 33984 are described in WO 2005/035486 and in unpublished international application PCT/EP2006/068469.

The compounds of the formula I, and their agriculturally acceptable salts are highly active against animal pest, i.e. harmful arthropodes and nematodes, especially against difficult to control insects and acaridae.

Accordingly, the present invention relates to 3-amino-1,2-benzisothiazole compounds of the general formula I and to their agriculturally useful salts.

Moreover, the present invention relates to:

agricultural compositions comprising such an amount of at least one 3-amino-1,2-benzisothiazole derivative of the formula I and/or one enantiomer, diastereomer or agriculturally acceptable salt thereof and at least one inert liquid and/or solid agronomically acceptable carrier and, if desired, at least one surfactant;

the use of compounds I and/or one enantiomer, diastereomer or agriculturally acceptable salt thereof for combating animal pests;

a method of combating animal pests which comprises contacting the animal pests, their habit, breeding ground, food supply, plant, seed, soil, area, material or environment in which the animal pests are growing or may grow, or the materials, plants, seeds, soils, surfaces or spaces to be protected from animal attack or infestation with a pesticidally effective amount of at least one compound of the formula I and/or one enantiomer, diastereomer or agriculturally acceptable salt thereof, as defined herein;

a method for protecting crops from attack or infestation by animal pests, which comprises contacting a crop with a pesticidally effective amount of at least one compound of the formula I and/or at least one salt thereof.

a method for protecting seeds from soil insects and of the seedlings' roots and shoots from soil and foliar insects comprising contacting the seeds before sowing and/or after pregermination with at least one 3-amino-1,2-benzisothiazole compound of the formula I and/or one enantiomer, diastereomer or agriculturally acceptable salt thereof or a composition comprising at least such one compound; and to seeds comprising an 3-amino-1,2-benzisothiazole compound of the formula I and/or one enantiomer, diastereomer or agriculturally acceptable salt of thereof.

Salts of the compounds of the formula I are preferably agriculturally acceptable salts. They can be formed in a customary method, e.g. by reacting the compound with an acid of the anion in question if the compound of formula I has a basic functionality or by reacting an acidic compound of formula I with a suitable base.

Suitable agriculturally useful salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethyl-ammonium, bis(2-hydroxyethyl)ammonium, benzyltrimethylammonium and benzyltriethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting the compounds of the formulae I with an acid of the corresponding anion, preferably of hydrochloric acid, hydrobromic acid, sulfuric acid, phosphoric acid or nitric acid.

The organic moieties mentioned in the above definitions of the variables are—like the term halogen—collective terms for individual listings of the individual group members. The prefix $C_n$-$C_m$ indicates in each case the possible number of carbon atoms in the group.

"Halogen" will be taken to mean fluoro, chloro, bromo and iodo.

The term "partially or fully halogenated" will be taken to mean that 1 or more, e.g. 1, 2, 3, 4 or 5 or all of the hydrogen atoms of a given radical have been replaced by a halogen atom, in particular by fluorine or chlorine.

The term "$C_n$-$C_m$-alkyl" as used herein (and also in $C_n$-$C_m$-alkylamino, di-$C_n$-$C_m$-alkylamino, $C_n$-$C_m$-alkylaminocarbonyl, di-($C_n$-$C_m$-alkylamino)carbonyl, $C_n$-$C_m$-alkylthio, $C_n$-$C_m$-alkylsulfinyl and $C_n$-$C_m$-alkylsulfonyl) refers to a branched or unbranched saturated hydrocarbon group having n to m, e.g. 1 to 10 carbon atoms, preferably 1 to 6 carbon atoms, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

The term "$C_n$-$C_m$-haloalkyl" as used herein (and also in $C_n$-$C_m$-haloalkylsulfinyl and $C_n$-$C_m$-haloalkylsulfonyl) refers to a straight-chain or branched alkyl group having n to m carbon atoms, e.g. 1 to 10 in particular 1 to 6 carbon atoms (as mentioned above), where some or all of the hydrogen atoms in these groups may be replaced by halogen atoms as mentioned above, for example $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like. The term $C_1$-$C_{10}$-haloalkyl in particular comprises $C_1$-$C_2$-fluoroalkyl, which is synonym with methyl or ethyl, wherein 1, 2, 3, 4 or 5 hydrogen atoms are substituted by fluorine atoms, such as fluoromethyl, difluoromethyl, trifluoromethyl, 1-fluoroethyl, 2-fluoroethyl, 2,2-difluoroethyl, 2,2,2-trifluoroethyl and pentafluoromethyl.

Similarly, "$C_n$-$C_m$-alkoxy" and "$C_n$-$C_m$-alkylthio" (or $C_n$-$C_m$-alkylsulfenyl, respectively) refer to straight-chain or branched alkyl groups having n to m carbon atoms, e.g. 1 to 10, in particular 1 to 6 or 1 to 4 carbon atoms (as mentioned above) bonded through oxygen or sulfur linkages, respectively, at any bond in the alkyl group. Examples include $C_1$-$C_4$-alkoxy such as methoxy, ethoxy, propoxy, isopropoxy, butoxy, sec-butoxy, isobutoxy and tert-butoxy, further $C_1$-$C_4$-alkylthio such as methylthio, ethylthio, propylthio, isopropylthio, and n-butylthio.

Accordingly, the terms "$C_n$-$C_m$-haloalkoxy" and "$C_n$-$C_m$-haloalkylthio" (or $C_n$-$C_m$-haloalkylsulfenyl, respectively) refer to straight-chain or branched alkyl groups having n to m carbon atoms, e.g. 1 to 10, in particular 1 to 6 or 1 to 4 carbon atoms (as mentioned above) bonded through oxygen or sulfur linkages, respectively, at any bond in the alkyl group, where some or all of the hydrogen atoms in these groups may be replaced by halogen atoms as mentioned above, for example $C_1$-$C_2$-haloalkoxy, such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy, further $C_1$-$C_2$-haloalkylthio, such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio and pentafluoroethylthio and the like. Similarly the terms $C_1$-$C_2$-fluoroalkoxy and $C_1$-$C_2$-fluoroalkylthio refer to $C_1$-$C_2$-fluoroalkyl which is bound to the remainder of the molecule via an oxygen atom or a sulfur atom, respectively.

The term "$C_2$-$C_m$-alkenyl" as used herein intends a branched or unbranched unsaturated hydrocarbon group having 2 to m, e.g. 2 to 10 or 2 to 6 carbon atoms and a double bond in any position, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term "$C_2$-$C_m$-alkynyl" as used herein refers to a branched or unbranched unsaturated hydrocarbon group having 2 to m, e.g. 2 to 10 or 2 to 6 carbon atoms and containing at least one triple bond, such as ethynyl, propynyl, 1-butynyl, 2-butynyl, and the like.

The term "$C_1$-$C_4$-alkoxy-$C_1$-$C_4$-alkyl" as used herein refers to alkyl having 1 to 4 carbon atoms, e.g. like specific examples mentioned above, wherein one hydrogen atom of the alkyl radical is replaced by an $C_1$-$C_4$-alkoxy group.

The term "$C_1$-$C_4$-alkylthio-$C_1$-$C_4$-alkyl" as used herein refers to alkyl having 1 to 4 carbon atoms, wherein one hydrogen atom of the alkyl radical is replaced by a $C_1$-$C_4$-alkylthio group.

The term "$C_3$-$C_m$-cycloalkyl" as used herein refers to a monocyclic 3- to m-membered saturated cycloaliphatic radicals, e.g. cyclopropyl, cyclobutyl, cyclopentyl, cyclohexyl, cycloheptyl, cyclooctyl and cyclodecyl.

The term "aryl" as used herein refers to an aromatic hydrocarbon radical such as naphthyl or phenyl, in particular phenyl.

The term "aryl-$C_1$-$C_4$-alkyl" as used herein refers to an aromatic hydrocarbon radical, which is bound to the remainder of the molecule via a $C_1$-$C_4$-alkylene group, examples comprise benzyl, 1-phenylethyl or 2-phenylethyl.

The term "3- to 7-membered heterocyclyl" as used herein (and also in heterocyclyl-$C_1$-$C_4$-alkyl) refers to a saturated or partially unsaturated non-aromatic heterocyclic radical having 3 to 7 ring members, wherein 1, 2 or 3 ring members are heteroatoms selected from O, N and S or heteroatom groups, selected from S=O, S(O)$_2$ or N—R with R being H or alkyl. Examples for non-aromatic rings include azetidiyl, pyrrolidinyl, pyrazolinyl, imidazolinyl, pyrrolinyl, pyrazolinyl, imidazolinyl, tetrahydrofuranyl, dihydrofuranyl, 1,3-dioxolanyl, dioxolenyl, thiolanyl, dihydrothienyl, oxazolidinyl, isoxazolidinyl, oxazolinyl, isoxazolinyl, thiazolinyl, isothiazolinyl, thiazolidinyl, isothiazolidinyl, oxathiolanyl, piperidinyl, piperazinyl, pyranyl, dihydropyranyl, tetrahydropyranyl, dioxanyl, thiopyranyl, dihydrothiopyranyl, tetrahydrothiopyranyl, morpholinyl, thiazinyl and the like.

The term "3- to 7-membered heteroaryl" as used herein (and also in heteroaryl-$C_1$-$C_4$-alkyl) refers to an aromatic heterocyclic radical having 3 to 7 ring members, wherein 1, 2 or 3 ring members are heteroatoms selected from O, N and S or heteroatom groups, selected from S=O, S(O)$_2$ or N—R with R being H or alkyl. Examples for monocyclic 3- to 7-membered heteroaromatic rings include triazinyl, pyrazinyl, pyrimidyl, pyridazinyl, pyridyl, thienyl, furyl, pyrrolyl, pyrazolyl, imidazolyl, triazolyl, tetrazolyl, thiazolyl, oxazolyl, thiadiazolyl, oxadiazolyl, isothiazolyl and isoxazolyl.

The terms "heterocyclyl-$C_1$-$C_4$-alkyl" and "heteroaryl-$C_1$-$C_4$-alkyl" as used herein refer to a non-aromatic or aromatic heterocyclic radical, which is bound to the remainder of the molecule via a $C_1$-$C_4$-alkylene group.

With respect to the use according to the invention of the 3-amino-1,2-benzisothiazole compounds of formula I, particular preference is given to the following meanings of the substituents and variables, in each case on their own or in combination:

Preferred are 3-amino-1,2 benzisothiazole compounds of formula I, wherein n is 2. Preferred are also 3-amino-1,2 benzisothiazole compounds of formula I, wherein n is 1. Preferred are equally 3-amino-1,2 benzisothiazole compounds of formula I, wherein n is 0.

Preferred are 3-amino-1,2 benzisothiazole compounds of formula I, wherein $R^1$ is selected from $C_1$-$C_6$-alkoxy or $C_1$-$C_6$-haloalkoxy, in particular wherein $R^1$ is selected from $C_1$-$C_6$-fluoroalkoxy or $C_1$-$C_6$-chloroalkoxy, such as trifluoromethoxy or trichloromethoxy.

Preferred are 3-amino-1,2 benzisothiazole compounds of formula I, wherein $R^2$, $R^3$ and $R^4$ are independently of one another selected from the group consisting of hydrogen, F, Cl, Br or J.

Preferred are also 3-amino-1,2 benzisothiazole compounds of formula I, wherein $R^2$, $R^3$ and $R^4$ are independently of one hydrogen or fluoro.

Especially preferred are also 3-amino-1,2 benzisothiazole compounds of formula I, wherein $R^2$, $R^3$ and $R^4$ are hydrogen Preferred are 3-amino-1,2 benzisothiazole compounds of formula I, wherein $R^5$ is selected from $C_1$-$C_6$-alkyl, which may be unsubstituted, partially or fully halogenated and/or may carry 1-4 radicals selected from the group consisting of $C_1$-$C_{10}$-alkoxy, $C_1$-$C_{10}$-alkylthio, $C_1$-$C_{10}$-alkylsulfinyl, $C_1$-$C_{10}$-alkylsulfonyl, $C_1$-$C_{10}$-haloalkoxy, $C_1$-$C_{10}$-haloalkylthio, ($C_1$-$C_{10}$-alkoxy)carbonyl, cyano, nitro, amino, ($C_1$-$C_{10}$-alkyl)amino, di-($C_1$-$C_{10}$-alkyl)amino, $C_3$-$C_{10}$-cycloalkyl and phenyl, it being possible for phenyl to be unsubstituted, partially or fully halogenated and/or to carry 1-3 substituents selected from the group consisting of CN, $C_1$-$C_6$-alkyl, $C_1$-$C_6$-haloalkyl, $C_1$-$C_6$-alkoxy, $C_1$-$C_6$-haloalkoxy.

Especially preferred are also 3-amino-1,2 benzisothiazole compounds of formula I, wherein $R^5$ is hydrogen and n is 1 or 2.

In another embodiment of the invention the compounds of formula I have the following preferred combinations of $R^1$, $R^2$; $R^3$, $R^4$ and $R^5$:

3-amino-1,2 benzisothiazole compounds of formula I, wherein $R^1$ is preferably selected from $C_1$-$C_6$-alkoxy or $C_1$-$C_6$-haloalkoxy and $R^2$, $R^3$ and $R^4$ are independently of one another preferably selected from the group consisting of hydrogen, F, Cl, Br or J.

3-amino-1,2 benzisothiazole compounds of formula I, wherein $R^1$ is preferably selected from $C_1$-$C_6$-alkoxy or $C_1$-$C_6$-haloalkoxy and $R^2$, $R^3$ and $R^4$ are preferably hydrogen.

3-amino-1,2 benzisothiazole compounds of formula I wherein $R^1$ is preferably selected from $C_1$-$C_6$-alkoxy or $C_1$-$C_6$-haloalkoxy, $R^2$, $R^3$ and $R^4$ are preferably independently of one another selected from the group consisting of hydrogen, F, Cl, Br or J, and $R^5$ is preferably selected from $C_1$-$C_6$-alkyl, which may be unsubstituted, partially or fully halogenated and/or may carry 1-4 radicals selected from the group consisting of $C_1$-$C_{10}$-alkoxy, $C_1$-$C_{10}$-alkylsulfinyl, $C_1$-$C_{10}$-haloalkoxy, $C_1$-$C_{10}$-haloalkylthio, ($C_1$-$C_{10}$-alkoxy)carbonyl, cyano, nitro, amino, ($C_1$-$C_{10}$-alkyl)amino, di-($C_1$-$C_{10}$-alkyl)amino, $C_3$-$C_{10}$-cycloalkyl and phenyl, it being possible for phenyl to be unsubstituted, partially or fully halogenated and/or to carry 1-3 substituents selected from the group consisting of CN, $C_1$-$C_6$-alkyl, $C_1$-$C_6$-haloalkyl, $C_1$-$C_6$-alkoxy, $C_1$-$C_6$-haloalkoxy.

PREPARATION METHODS

P.0. 3-Amino-benzisothiazole

3-Amino-benzisothiazoles (P0-I) can be prepared by heating a suitably substituted disulfide (P0-II) together with an amine and an oxidizing agent such as dimethylsulfoxide (DMSO) in a polar solvent such as isopropanol as described by S. W. Walinsky et al. in Organic Process Research & Development 1999, 3, 126-130.

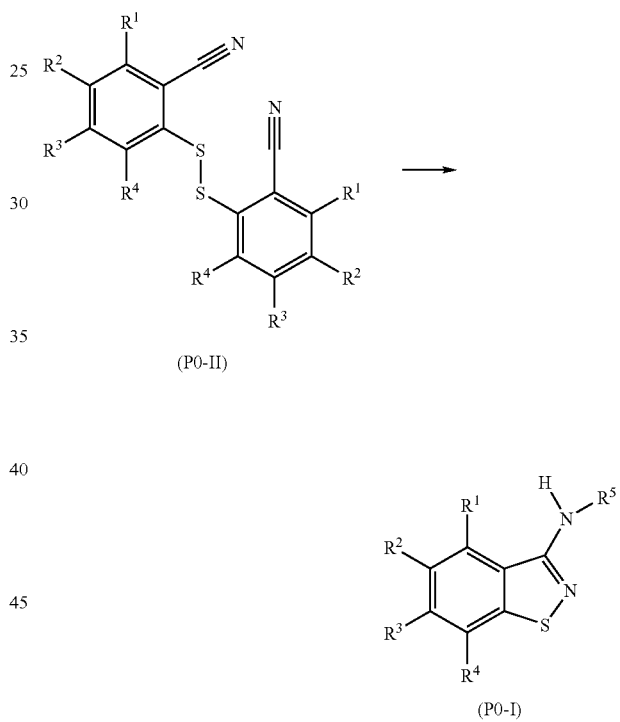

The 2-cyano-disulfides (P0-II) can be prepared from the corresponding thiophenols (P0-III) by using oxidizing agents such as dimethylsulfoxid (DMSO) as reported by H. Boerzel et al. in Inorganic Chemistry 2003, 1604-1615.

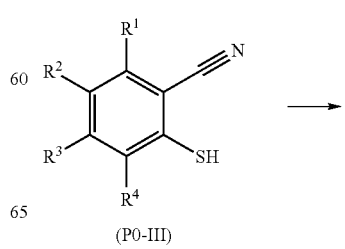

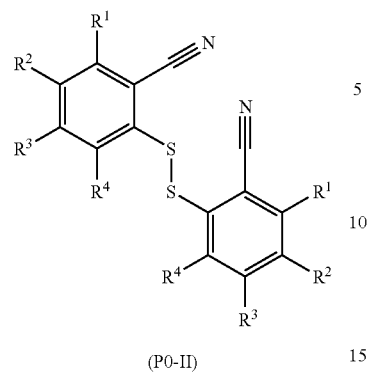

(P0-II)

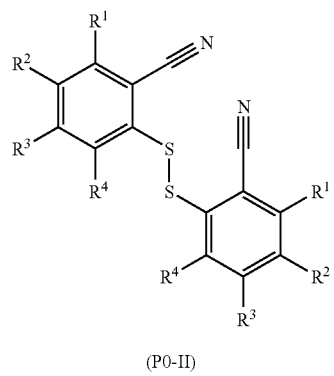

(P0-II)

2-cyano-thiophenols (P0-III) can be prepared from benzisothiazoles (P0-IV) by treatment with strong bases such as NaOCH$_3$ as described by J. Markert et al. in Liebigs Annalen d. Chemie 1980, 768-778.

2-cyano-anilines (P0-VI) can be prepared from 2-cyano-nitrobenzenes (P0-VII) with a reducing agent such as iron as described by D. H. Klaubert in J. Med. Chem. 1981, 24, 742-748.

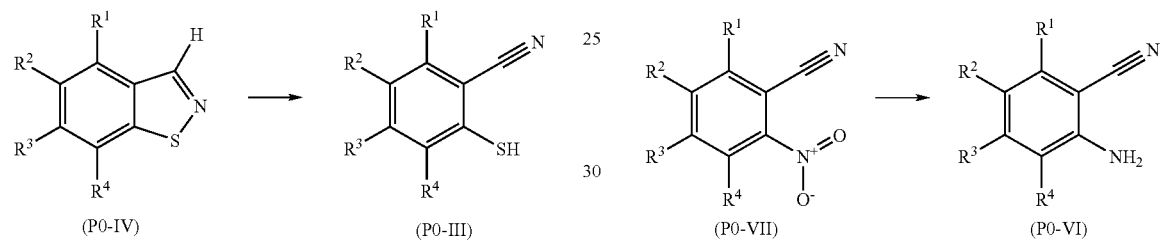

(P0-IV)　　(P0-III)　　(P0-VII)　　(P0-VI)

Said article also describes the synthesis of substituted benzisothiazoles (P0-IV) from 2-chloro-benzaldahydes (P0-V) via reaction with sulfur and ammonia.

Alternatively 3-amino-1,2-benzisothiazoles (P0-1) can also be prepared from 3-chlorobenzo[d]isothiazole (P0-VIIIa) as described by H. Boeshagen et al. in Justus Liebig Annalen der Chemie, 1977, 20.

Alternatively further 3-amino-1,2-benzisothiazoles (P0-I) can be obtained from trifluoro-methanesulfonic acid benzo[d]isothiazol-3-yl ester (P0-VIIIb) in analogy to U.S. Pat. No. 5,359,068 by reaction of said compounds with amines. The latter reference also describes the trifluoro-methanesulfonic acid benzo[d]isothiazol-3-yl ester (P0-VIIIb) obtained from benzisothiazolones.

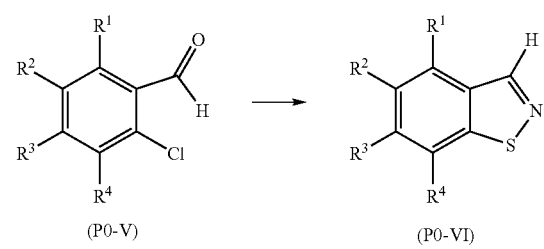

(P0-V)　　(P0-VI)

The Chloro-benzo[d]isothiazoles (P0-VIIIa) can be obtained from benzisothiazolones (P0-IX) by reaction with a chlorinating agent such as PCl$_3$ (described by J. P. Yevich et al. in Journal of Medicinal Chemistry 1986, 29, 359-369) or PCl$_3$/PCl$_5$ (S. G. Zlutin et al. Journal of Organic Chemistry 2000, 65, 8439-8443).

Alternatively, the 2-cyano-disulfides (P0-II) can be prepared from 2-cyano-anilines (P0-VI) via diazotation and subsequent reaction of the diazonium-salt with Na$_2$S and sulfur as described by V. M. Negrimovsky et al. in Phosphorus, Sulfur & The Related Elements 1995, 104, 161-167.

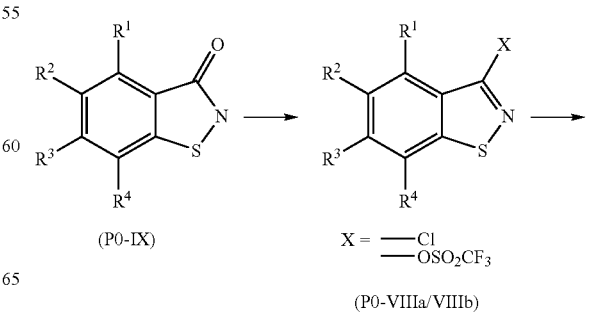

(P0-IX)　　X = —Cl
　　　　　　　　—OSO$_2$CF$_3$ (P0-VI)　　(P0-VIIIa/VIIIb)

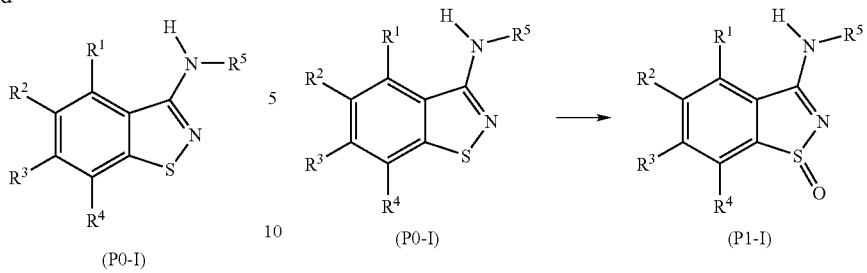

The last mentioned reference of S. G. Zlutin et al. also describes the synthesis of said benzisothiazolones (P0-IX) from 2-Benzylsulfanyl-benzamides (P0-X) via treatment with an oxidizing agent such as $SO_2Cl_2$.

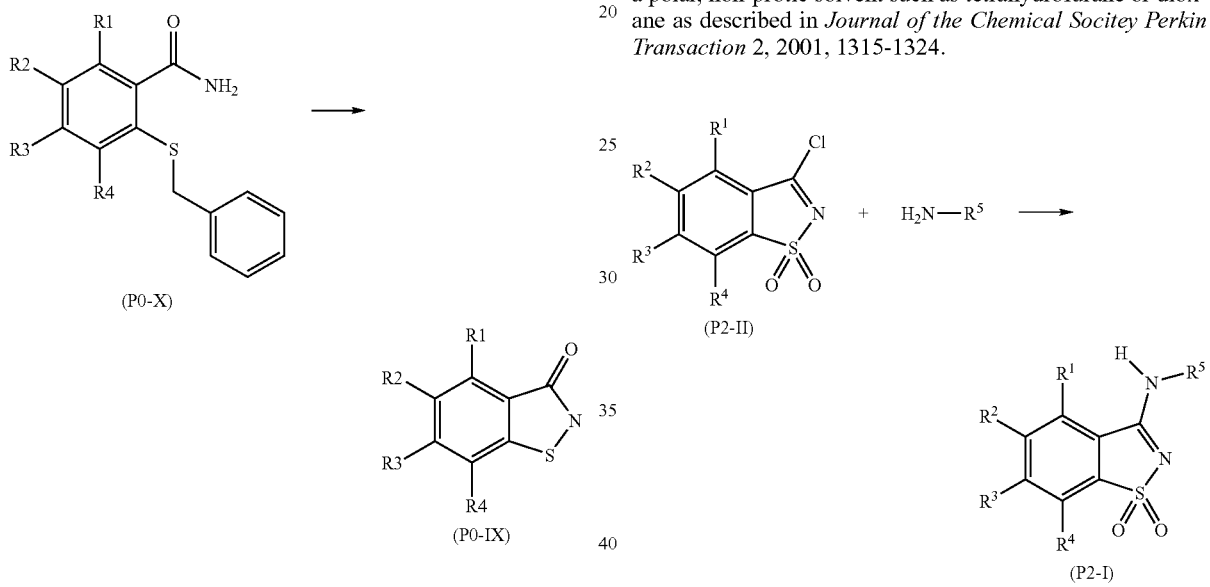

Alternatively, another method for preparing benzisothiazolones (P0-IX) from 2-(alkythio)benzonitriles (P0-XI) is described in EP-A 1081141.

P.1 Aminobenzisothiazole-1-monooxides

Aminobenzisothiazole (P0-I) can be oxidized in analogy to a procedure described in *Chemische Berichte*, 103, 3166-3181 to yield the mono-oxygenated species (P1-I). Suitable oxidizing reagents are e.g. $HNO_3$, $H_2O_2$/acetic acid or m-chlor-perbenzoic acid.

P.2 3-Aminobenzisothiazole-1,1-dioxides

3-Aminobenzisothiazole-1,1-dioxides (P2-I) can be obtained from suitably substituted 3-Chloro-benzo[d]isothiazole 1,1-dioxides (P2-II) by reaction with a primary amine in a polar, non-protic solvent such as tetrahydrofurane or dioxane as described in *Journal of the Chemical Socitey Perkin Transaction* 2, 2001, 1315-1324.

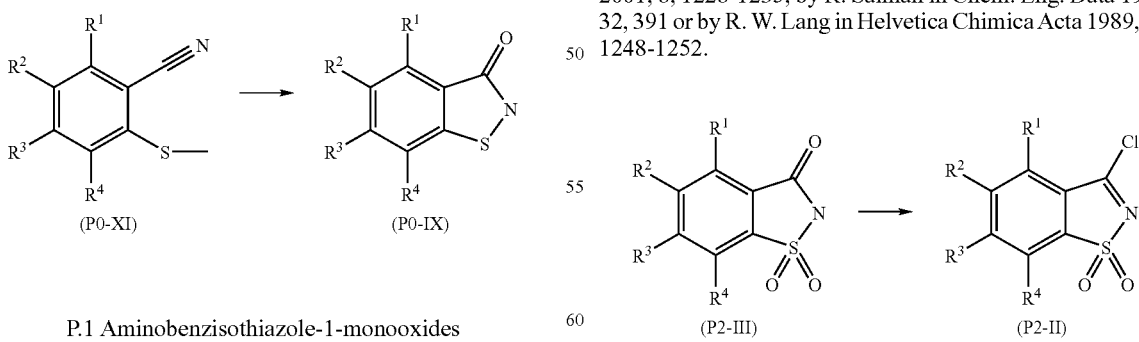

3-Chloro-benzo[d]isothiazole 1,1-dioxides (P2-II) can be prepared by the reaction of a suitably substituted saccharine (P2-III) with a chlorinating agent such as $ClCO_2CCl_3$, $PCl_5$/$POCl_3$ or $SOCl_2$ as described by D. Dopp et al. in Synthesis 2001, 8, 1228-1235, by R. Salman in Chem. Eng. Data 1987, 32, 391 or by R. W. Lang in Helvetica Chimica Acta 1989, 72, 1248-1252.

Substituted saccharines (P2-III) can be prepared via reaction of 2-chlorosulfonyl-benzoic acid esters (P2-IV) with ammonia as it is described by M. C. Bell et al. in Bioorganic & Medicinal Letters 1991, No. 12, 733-736 or M. L. Trudell et al. in Journal of Heterocyclic Chem. 2004, 41, 435f.

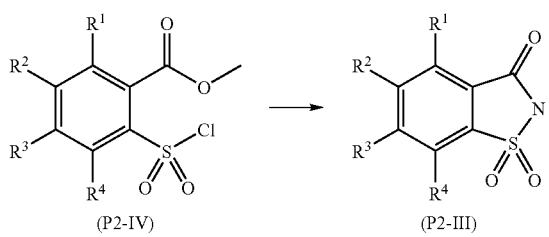

(P2-IV)    (P2-III)

The latter article also describes the synthesis of mentioned 2-chlorosulfonyl-benzoic acid esters (P2-IV) from the corresponding methyl anthranilates (P2-V) via diazotation and subsequent chlorosulfonation. A similar synthetic procedure is described by G. Hamprecht et al. in Chimia (2004), 58, 117-122.

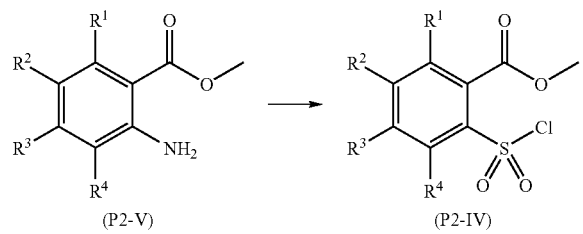

(P2-V)    (P2-IV)

In cases where the methyl anthranilates (P2-V) are not commercially available, they can be prepared from the corresponding 2-nitro benzoic acid methyl ester (P2-VI) via catalytic hydrogenation as mentioned by J. F. W. Keana et al. in Bioorganic & Medicinal Chemistry 11 (2003) 1769-1780.

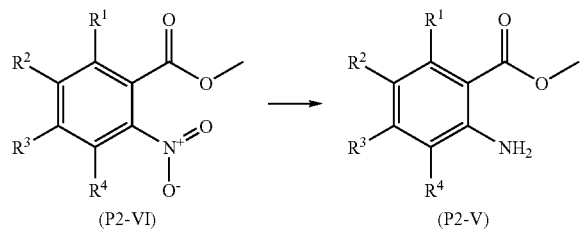

(P2-VI)    (P2-V)

Alternatively, saccharines (P2-II) can be prepared by cleavage of the corresponding N-t-butyl saccharines (P2-VII) via heating with a strong acid such as trifluoroacetic acid in a way described by K. F. Burri in Helvetica Chimica Acta 1990, 73, 69-80.

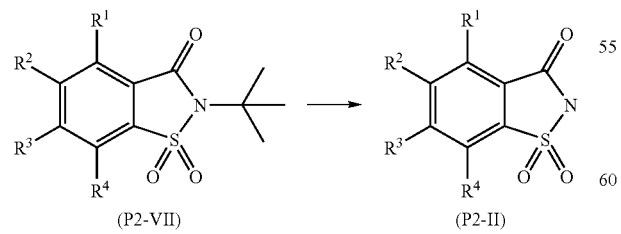

(P2-VII)    (P2-II)

N-t-butyl saccharines (P2-VII) can be obtained from the corresponding sulfonamides (P2-VIII) by directed ortho metallation with bases such as butyllithium or lithiumdiisopropylamide and subsequent trapping of the metallated species with carbon dioxide under ring-closure. The procedure is described by D. Becker et al. in Tetrahedron 1992, 2515-2522. The metallation can be carried out as described by N. Murugesan et al. in J. Med. Chem. 1998, 41, 5198-5218.

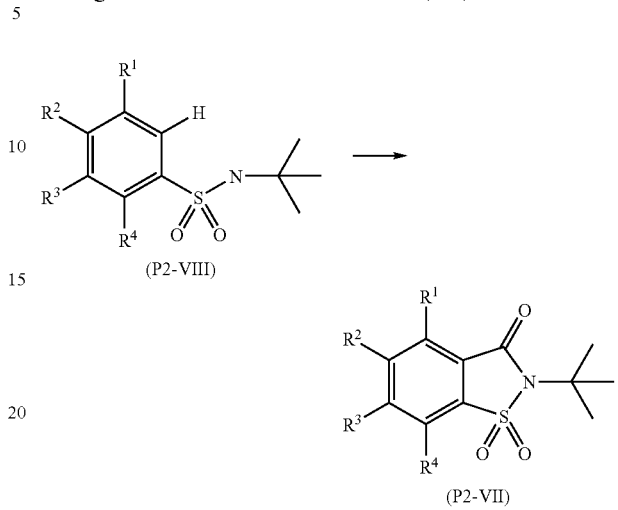

(P2-VIII)

(P2-VII)

Alternatively, 3-amino-1,2-benzisothiazole 1,1-dioxides (P2-I) can also be prepared from suitably substituted imidates (P2-IX) via a reaction with primary amines at elevated temperature. The reaction can be carried out either neat or in a suitable solvent, preferentially a polar, high-boiling solvent such as THF or dioxane. Preferentially, the reaction is carried out neat. In cases were the reaction is carried out neat, the preferred temperature is between room temperature and the boiling point of the respective amine. In cases were the reaction is carried out in a solvent, the preferred temperature is between room temperature and the boiling point of the respective solvent. The substituent $R^7$ in this method is preferentially an alkyl-substituent such as methyl or ethyl.

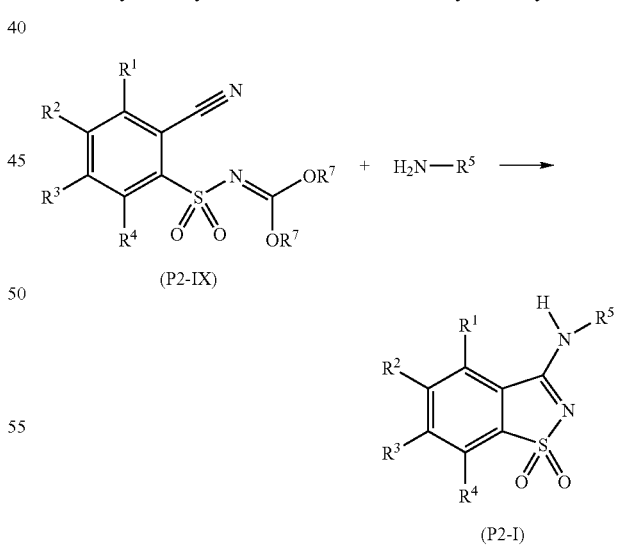

(P2-IX)

(P2-I)

Said imidates (P2-IX) can be obtained by reacting a 2-cyanobenzene sulfonamide (P2-X) with a carbonic acid orthoester in a process similarly described in Journal of Organic Chemistry 1963, 28, 2902-2903. Said cyanobenzene sulfonamides (P2-X) can be prepared as described in WO 2005/035486.

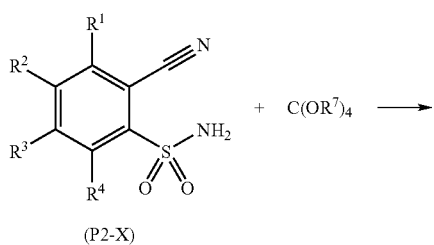

(P2-X)

(P2-IX)

P.3 3-Iminosaccharins

N-monosubstituted o-cyano-sulfonamides can be cyclized under basic conditions to the corresponding 3-iminosaccharins. As bases inorganic salts such as alkali carbonates are preferred. Preferred solvents are polar, water-miscible organic solvents such as dioxane or THF.

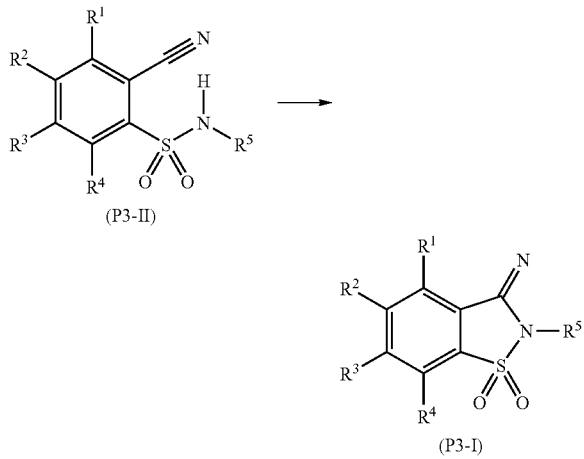

(P3-II)

(P3-I)

In the preparation methods described, the variables $R^1$, $R^2$, $R^3$, $R^4$, and $R^5$ have the meanings as defined above, in particular the meanings mentioned as being preferred.

If individual compounds cannot be prepared via the above-described routes, they can be prepared by derivatization of other compounds I or by customary modifications of the synthesis routes described.

The reaction mixtures are worked up in the customary manner, for example by mixing with water, separating the phases, and, if appropriate, purifying the crude products by chromatography, for example on alumina or silica gel. Some of the intermediates and end products may be obtained in the form of colorless or pale brown viscous oils, which are freed or purified from volatile components under reduced pressure and at moderately elevated temperature. If the intermediates and end products are obtained as solids, they may be purified by recrystallization or digestion.

Agriculturally acceptable salts of the compounds of formula I can be formed in a customary manner, e.g. by reaction with an acid of the anion in question.

Examples of preferred compounds of the formula I are given in the tables A1 to A126, wherein $R^1$, $R^2$, $R^3$ and $R^4$ are defined individually, and n and $R^5$ are defined also individually in following table A.

Table A1: Compounds of formula I, wherein each of $R^3$ and $R^4$ are H, $R^2$ is H, $R^1$ is $CH_3$ and wherein n and $R^5$ are as defined in one row of table A;

Table A2: Compounds of formula I, wherein each of $R^3$ and $R^4$ are H, $R^2$ is H, $R^1$ is $C_2H_5$ and wherein n and $R^5$ are as defined in one row of table A;

Table A3: Compounds of formula I, wherein each of $R^3$ and $R^4$ are H, $R^2$ is H, $R^1$ is $CF_3$ and wherein n and $R^5$ are as defined in one row of table A;

Table A4: Compounds of formula I, wherein each of $R^3$ and $R^4$ are H, $R^2$ is H, $R^1$ is $OCH_3$ and wherein n and $R^5$ are as defined in one row of table A;

Table A5: Compounds of formula I, wherein each of $R^3$ and $R^4$ are H, $R^2$ is H, $R^1$ is $OC_2H_5$ and wherein n and $R^5$ are as defined in one row of table A;

Table A6: Compounds of formula I, wherein each of $R^3$ and $R^4$ are H, $R^2$ is H, $R^1$ is $OCF_3$ and wherein n and $R^5$ are as defined in one row of table A;

Table A7: Compounds of formula I, wherein each of $R^3$ and $R^4$ are H, $R^2$ is H, $R^1$ is $OCHF_2$ and wherein n and $R^5$ are as defined in one row of table A;

Table A8: Compounds of formula I, wherein each of $R^3$ and $R^4$ are H, $R^2$ is H, $R^1$ is $OCClF_2$ and wherein n and $R^5$ are as defined in one row of table A;

Table A9: Compounds of formula I, wherein each of $R^3$ and $R^4$ are H, $R^2$ is H, $R^1$ is $OCF_2CHClF$ and wherein n and $R^5$ are as defined in one row of table A;

Table A10: Compounds of formula I, wherein each of $R^3$ and $R^4$ are H, $R^2$ is F, $R^1$ is $CH_3$ and wherein n and $R^5$ are as defined in one row of table A;

Table A11: Compounds of formula I, wherein each of $R^3$ and $R^4$ are H, $R^2$ is F, $R^1$ is $C_2H_5$ and wherein n and $R^5$ are as defined in one row of table A;

Table A12: Compounds of formula I, wherein each of $R^3$ and $R^4$ are H, $R^2$ is F, $R^1$ is $CF_3$ and wherein n and $R^5$ are as defined in one row of table A;

Table A13: Compounds of formula I, wherein each of $R^3$ and $R^4$ are H, $R^2$ is F, $R^1$ is $OCH_3$ and wherein n and $R^5$ are as defined in one row of table A;

Table A14: Compounds of formula I, wherein each of $R^3$ and $R^4$ are H, $R^2$ is F, $R^1$ is $OC_2H_5$ and wherein n and $R^5$ are as defined in one row of table A;

Table A15: Compounds of formula I, wherein each of $R^3$ and $R^4$ are H, $R^2$ is F, $R^1$ is $OCF_3$ and wherein n and $R^5$ are as defined in one row of table A;

Table A16: Compounds of formula I, wherein each of $R^3$ and $R^4$ are H, $R^2$ is F, $R^1$ is $OCHF_2$ and wherein n and $R^5$ are as defined in one row of table A;

Table A17: Compounds of formula I, wherein each of $R^3$ and $R^4$ are H, $R^2$ is F, $R^1$ is $OCClF_2$ and wherein n and $R^5$ are as defined in one row of table A;

Table A18: Compounds of formula I, wherein each of $R^3$ and $R^4$ are H, $R^2$ is F, $R^1$ is $OCF_2CHClF$ and wherein n and $R^5$ are as defined in one row of table A;

Table A19: Compounds of formula I, wherein each of $R^3$ and $R^4$ are H, $R^2$ is Cl, $R^1$ is $CH_3$ and wherein n and $R^5$ are as defined in one row of table A;

Table A20: Compounds of formula I, wherein each of $R^3$ and $R^4$ are H, $R^2$ is Cl, $R^1$ is $C_2H_5$ and wherein n and $R^5$ are as defined in one row of table A;

Table A21: Compounds of formula I, wherein each of $R^3$ and $R^4$ are H, $R^2$ is Cl, $R^1$ is $CF_3$ and wherein n and $R^5$ are as defined in one row of table A;

Table A22: Compounds of formula I, wherein each of $R^3$ and $R^4$ are H, $R^2$ is Cl, $R^1$ is $OCH_3$ and wherein n and $R^5$ are as defined in one row of table A;

Table A23: Compounds of formula I, wherein each of $R^3$ and $R^4$ are H, $R^2$ is Cl, $R^1$ is $OC_2H_5$ and wherein n and $R^5$ are as defined in one row of table A;

Table A24: Compounds of formula I, wherein each of $R^3$ and $R^4$ are H, $R^2$ is Cl, $R^1$ is $OCF_3$ and wherein n and $R^5$ are as defined in one row of table A;

Table A25: Compounds of formula I, wherein each of $R^3$ and $R^4$ are H, $R^2$ is Cl, $R^1$ is $OCHF_2$ and wherein n and $R^5$ are as defined in one row of table A;

Table A26: Compounds of formula I, wherein each of $R^3$ and $R^4$ are H, $R^2$ is Cl, $R^1$ is $OCClF_2$ and wherein n and $R^5$ are as defined in one row of table A;

Table A27: Compounds of formula I, wherein each of $R^3$ and $R^4$ are H, $R^2$ is Cl, $R^1$ is $OCF_2CHClF$ and wherein n and $R^5$ are as defined in one row of table A;

Table A28: Compounds of formula I, wherein each of $R^3$ and $R^4$ are H, $R^2$ is Br, $R^1$ is $CH_3$ and wherein n and $R^5$ are as defined in one row of table A;

Table A29: Compounds of formula I, wherein each of $R^3$ and $R^4$ are H, $R^2$ is Br, $R^1$ is $C_2H_5$ and wherein n and $R^5$ are as defined in one row of table A;

Table A30: Compounds of formula I, wherein each of $R^3$ and $R^4$ are H, $R^2$ is Br, $R^1$ is $CF_3$ and wherein n and $R^5$ are as defined in one row of table A;

Table A31: Compounds of formula I, wherein each of $R^3$ and $R^4$ are H, $R^2$ is Br, $R^1$ is $OCH_3$ and wherein n and $R^5$ are as defined in one row of table A;

Table A32: Compounds of formula I, wherein each of $R^3$ and $R^4$ are H, $R^2$ is Br, $R^1$ is $OC_2H_5$ and wherein n and $R^5$ are as defined in one row of table A;

Table A33: Compounds of formula I, wherein each of $R^3$ and $R^4$ are H, $R^2$ is Br, $R^1$ is $OCF_3$ and wherein n and $R^5$ are as defined in one row of table A;

Table A34: Compounds of formula I, wherein each of $R^3$ and $R^4$ are H, $R^2$ is Br, $R^1$ is $OCHF_2$ and wherein n and $R^5$ are as defined in one row of table A;

Table A35: Compounds of formula I, wherein each of $R^3$ and $R^4$ are H, $R^2$ is Br, $R^1$ is $OCClF2$ and wherein n and $R^5$ are as defined in one row of table A;

Table A36: Compounds of formula I, wherein each of $R^3$ and $R^4$ are H, $R^2$ is Br, $R^1$ is $OCF_2CHClF$ and wherein n and $R^5$ are as defined in one row of table A;

Table A37: Compounds of formula I, wherein each of $R^3$ and $R^4$ are H, $R^2$ is J, $R^1$ is $CH_3$ and wherein n and $R^5$ are as defined in one row of table A;

Table A38: Compounds of formula I, wherein each of $R^3$ and $R^4$ are H, $R^2$ is J, $R^1$ is $C_2H_5$ and wherein n and $R^5$ are as defined in one row of table A;

Table A39: Compounds of formula I, wherein each of $R^3$ and $R^4$ are H, $R^2$ is J, $R^1$ is $CF_3$ and wherein n and $R^5$ are as defined in one row of table A;

Table A40: Compounds of formula I, wherein each of $R^3$ and $R^4$ are H, $R^2$ is J, $R^1$ is $OCH_3$ and wherein n and $R^5$ are as defined in one row of table A;

Table A41: Compounds of formula I, wherein each of $R^3$ and $R^4$ are H, $R^2$ is J, $R^1$ is $OC_2H_5$ and wherein n and $R^5$ are as defined in one row of table A;

Table A42: Compounds of formula I, wherein each of $R^3$ and $R^4$ are H, $R^2$ is J, $R^1$ is $OCF_3$ and wherein n and $R^5$ are as defined in one row of table A;

Table A43: Compounds of formula I, wherein each of $R^3$ and $R^4$ are H, $R^2$ is J, $R^1$ is $OCHF_2$ and wherein n and $R^5$ are as defined in one row of table A;

Table A44: Compounds of formula I, wherein each of $R^3$ and $R^4$ are H, $R^2$ is J, $R^1$ is $OCClF2$ and wherein n and $R^5$ are as defined in one row of table A;

Table A45: Compounds of formula I, wherein each of $R^3$ and $R^4$ are H, $R^2$ is J, $R^1$ is $OCF_2CHClF$ and wherein n and $R^5$ are as defined in one row of table A;

Table A46: Compounds of formula I, wherein each of $R^2$ and $R^4$ are H, $R^3$ is F, $R^1$ is $CH_3$ and wherein n and $R^5$ are as defined in one row of table A;

Table A47: Compounds of formula I, wherein each of $R^2$ and $R^4$ are H, $R^3$ is F, $R^1$ is $C_2H_5$ and wherein n and $R^5$ are as defined in one row of table A;

Table A48: Compounds of formula I, wherein each of $R^2$ and $R^4$ are H, $R^3$ is F, $R^1$ is $CF_3$ and wherein n and $R^5$ are as defined in one row of table A;

Table A49: Compounds of formula I, wherein each of $R^2$ and $R^4$ are H, $R^3$ is F, $R^1$ is $OCH_3$ and wherein n and $R^5$ are as defined in one row of table A;

Table A50: Compounds of formula I, wherein each of $R^2$ and $R^4$ are H, $R^3$ is F, $R^1$ is $OC_2H_5$ and wherein n and $R^5$ are as defined in one row of table A;

Table A51: Compounds of formula I, wherein each of $R^2$ and $R^4$ are H, $R^3$ is F, $R^1$ is $OCF_3$ and wherein n and $R^5$ are as defined in one row of table A;

Table A52: Compounds of formula I, wherein each of $R^2$ and $R^4$ are H, $R^3$ is F, $R^1$ is $OCHF_2$ and wherein n and $R^5$ are as defined in one row of table A;

Table A53: Compounds of formula I, wherein each of $R^2$ and $R^4$ are H, $R^3$ is F, $R^1$ is $OCClF_2$ and wherein n and $R^5$ are as defined in one row of table A;

Table A54: Compounds of formula I, wherein each of $R^2$ and $R^4$ are H, $R^3$ is F, $R^1$ is $OCF_2CHClF$ and wherein n and $R^5$ are as defined in one row of table A;

Table A55: Compounds of formula I, wherein each of $R^2$ and $R^4$ are H, $R^3$ is Cl, $R^1$ is $CH_3$ and wherein n and $R^5$ are as defined in one row of table A;

Table A56: Compounds of formula I, wherein each of $R^2$ and $R^4$ are H, $R^3$ is Cl, $R^1$ is $C_2H_5$ and wherein n and $R^5$ are as defined in one row of table A;

Table A57: Compounds of formula I, wherein each of $R^2$ and $R^4$ are H, $R^3$ is Cl, $R^1$ is $CF_3$ and wherein n and $R^5$ are as defined in one row of table A;

Table A58: Compounds of formula I, wherein each of $R^2$ and $R^4$ are H, $R^3$ is Cl, $R^1$ is $OCH_3$ and wherein n and $R^5$ are as defined in one row of table A;

Table A59: Compounds of formula I, wherein each of $R^2$ and $R^4$ are H, $R^3$ is Cl, $R^1$ is $OC_2H_5$ and wherein n and $R^5$ are as defined in one row of table A;

Table A60: Compounds of formula I, wherein each of $R^2$ and $R^4$ are H, $R^3$ is Cl, $R^1$ is $OCF_3$ and wherein n and $R^5$ are as defined in one row of table A;

Table A61: Compounds of formula I, wherein each of $R^2$ and $R^4$ are H, $R^3$ is Cl, $R^1$ is $OCHF_2$ and wherein n and $R^5$ are as defined in one row of table A;

Table A62: Compounds of formula I, wherein each of $R^2$ and $R^4$ are H, $R^3$ is Cl, $R^1$ is $OCClF_2$ and wherein n and $R^5$ are as defined in one row of table A;

Table A63: Compounds of formula I, wherein each of $R^2$ and $R^4$ are H, $R^3$ is Cl, $R^1$ is $OCF_2CHClF$ and wherein n and $R^5$ are as defined in one row of table A;

Table A64: Compounds of formula I, wherein each of $R^2$ and $R^4$ are H, $R^3$ is Br, $R^1$ is $CH_3$ and wherein n and $R^5$ are as defined in one row of table A;

Table A65: Compounds of formula I, wherein each of $R^2$ and $R^4$ are H, $R^3$ is Br, $R^1$ is $C_2H_5$ and wherein n and $R^5$ are as defined in one row of table A;

Table A66: Compounds of formula I, wherein each of $R^2$ and $R^4$ are H, $R^3$ is Br, $R^1$ is $CF_3$ and wherein n and $R^5$ are as defined in one row of table A;

Table A67: Compounds of formula I, wherein each of $R^2$ and $R^4$ are H, $R^3$ is Br, $R^1$ is $OCH_3$ and wherein n and $R^5$ are as defined in one row of table A;

Table A68: Compounds of formula I, wherein each of $R^2$ and $R^4$ are H, $R^3$ is Br, $R^1$ is $OC_2H_5$ and wherein n and $R^5$ are as defined in one row of table A;

Table A69: Compounds of formula I, wherein each of $R^2$ and $R^4$ are H, $R^3$ is Br, $R^1$ is $OCF_3$ and wherein n and $R^5$ are as defined in one row of table A;

Table A70: Compounds of formula I, wherein each of $R^2$ and $R^4$ are H, $R^3$ is Br, $R^1$ is $OCHF_2$ and wherein n and $R^5$ are as defined in one row of table A;

Table A71: Compounds of formula I, wherein each of $R^2$ and $R^4$ are H, $R^3$ is Br, $R^1$ is $OCClF_2$ and wherein n and $R^5$ are as defined in one row of table A;

Table A72: Compounds of formula I, wherein each of $R^2$ and $R^4$ are H, $R^3$ is Br, $R^1$ is $OCF_2CHClF$ and wherein n and $R^5$ are as defined in one row of table A;

Table A73: Compounds of formula I, wherein each of $R^2$ and $R^4$ are H, $R^3$ is J, $R^1$ is $CH_3$ and wherein n and $R^5$ are as defined in one row of table A;

Table A74: Compounds of formula I, wherein each of $R^2$ and $R^4$ are H, $R^3$ is J, $R^1$ is $C_2H_5$ and wherein n and $R^5$ are as defined in one row of table A;

Table A75: Compounds of formula I, wherein each of $R^2$ and $R^4$ are H, $R^3$ is J, $R^1$ is $CF_3$ and wherein n and $R^5$ are as defined in one row of table A;

Table A76: Compounds of formula I, wherein each of $R^2$ and $R^4$ are H, $R^3$ is J, $R^1$ is $OCH_3$ and wherein n and $R^5$ are as defined in one row of table A;

Table A77: Compounds of formula I, wherein each of $R^2$ and $R^4$ are H, $R^3$ is J, $R^1$ is $OC_2H_5$ and wherein n and $R^5$ are as defined in one row of table A;

Table A78: Compounds of formula I, wherein each of $R^2$ and $R^4$ are H, $R^3$ is J, $R^1$ is $OCF_3$ and wherein n and $R^5$ are as defined in one row of table A;

Table A79: Compounds of formula I, wherein each of $R^2$ and $R^4$ are H, $R^3$ is J, $R^1$ is $OCHF_2$ and wherein n and $R^5$ are as defined in one row of table A;

Table A80: Compounds of formula I, wherein each of $R^2$ and $R^4$ are H, $R^3$ is J, $R^1$ is $OCClF_2$ and wherein n and $R^5$ are as defined in one row of table A;

Table A81: Compounds of formula I, wherein each of $R^2$ and $R^4$ are H, $R^3$ is J, $R^1$ is $OCF_2CHClF$ and wherein n and $R^5$ are as defined in one row of table A;

Table A82: Compounds of formula I, wherein each of $R^3$ and $R^2$ are H, $R^4$ is F, $R^1$ is $CH_3$ and wherein n and $R^5$ are as defined in one row of table A;

Table A83: Compounds of formula I, wherein each of $R^3$ and $R^2$ are H, $R^4$ is F, $R^1$ is $C_2H_5$ and wherein n and $R^5$ are as defined in one row of table A;

Table A84: Compounds of formula I, wherein each of $R^3$ and $R^2$ are H, $R^4$ is F, $R^1$ is $CF_3$ and wherein n and $R^5$ are as defined in one row of table A;

Table A85: Compounds of formula I, wherein each of $R^3$ and $R^2$ are H, $R^4$ is F, $R^1$ is $OCH_3$ and wherein n and $R^5$ are as defined in one row of table A;

Table A86: Compounds of formula I, wherein each of $R^3$ and $R^2$ are H, $R^4$ is F, $R^1$ is $OC_2H_5$ and wherein n and $R^5$ are as defined in one row of table A;

Table A87: Compounds of formula I, wherein each of $R^3$ and $R^2$ are H, $R^4$ is F, $R^1$ is $OCF_3$ and wherein n and $R^5$ are as defined in one row of table A;

Table A88: Compounds of formula I, wherein each of $R^3$ and $R^2$ are H, $R^4$ is F, $R^1$ is $OCHF_2$ and wherein n and $R^5$ are as defined in one row of table A;

Table A89: Compounds of formula I, wherein each of $R^3$ and $R^2$ are H, $R^4$ is F, $R^1$ is $OCClF_2$ and wherein n and $R^5$ are as defined in one row of table A;

Table A90: Compounds of formula I, wherein each of $R^3$ and $R^2$ are H, $R^4$ is F, $R^1$ is $OCF_2CHClF$ and wherein n and $R^5$ are as defined in one row of table A;

Table A91: Compounds of formula I, wherein each of $R^3$ and $R^2$ are H, $R^4$ is Cl, $R^1$ is $CH_3$ and wherein n and $R^5$ are as defined in one row of table A;

Table A92: Compounds of formula I, wherein each of $R^3$ and $R^2$ are H, $R^4$ is Cl, $R^1$ is $C_2H_5$ and wherein n and $R^5$ are as defined in one row of table A;

Table A93: Compounds of formula I, wherein each of $R^3$ and $R^2$ are H, $R^4$ is Cl, $R^1$ is $CF_3$ and wherein n and $R^5$ are as defined in one row of table A;

Table A94: Compounds of formula I, wherein each of $R^3$ and $R^2$ are H, $R^4$ is Cl, $R^1$ is $OCH_3$ and wherein n and $R^5$ are as defined in one row of table A;

Table A95: Compounds of formula I, wherein each of $R^3$ and $R^2$ are H, $R^4$ is Cl, $R^1$ is $OC_2H_5$ and wherein n and $R^5$ are as defined in one row of table A;

Table A96: Compounds of formula I, wherein each of $R^3$ and $R^2$ are H, $R^4$ is Cl, $R^1$ is $OCF_3$ and wherein n and $R^5$ are as defined in one row of table A;

Table A97: Compounds of formula I, wherein each of $R^3$ and $R^2$ are H, $R^4$ is Cl, $R^1$ is $OCHF_2$ and wherein n and $R^5$ are as defined in one row of table A;

Table A98: Compounds of formula I, wherein each of $R^3$ and $R^2$ are H, $R^4$ is Cl, $R^1$ is $OCClF_2$ and wherein n and $R^5$ are as defined in one row of table A;

Table A99: Compounds of formula I, wherein each of $R^3$ and $R^2$ are H, $R^4$ is Cl, $R^1$ is $OCF_2CHClF$ and wherein n and $R^5$ are as defined in one row of table A;

Table A100: Compounds of formula I, wherein each of $R^3$ and $R^2$ are H, $R^4$ is Br, $R^1$ is $CH_3$ and wherein n and $R^5$ are as defined in one row of table A;

Table A101: Compounds of formula I, wherein each of $R^3$ and $R^2$ are H, $R^4$ is Br, $R^1$ is $C_2H_5$ and wherein n and $R^5$ are as defined in one row of table A;

Table A102: Compounds of formula I, wherein each of $R^3$ and $R^2$ are H, $R^4$ is Br, $R^1$ is $CF_3$ and wherein n and $R^5$ are as defined in one row of table A;

Table A103: Compounds of formula I, wherein each of $R^3$ and $R^2$ are H, $R^4$ is Br, $R^1$ is $OCH_3$ and wherein n and $R^5$ are as defined in one row of table A;

Table A104: Compounds of formula I, wherein each of $R^3$ and $R^2$ are H, $R^4$ is Br, $R^1$ is $OC_2H_5$ and wherein n and $R^5$ are as defined in one row of table A;

Table A105: Compounds of formula I, wherein each of $R^3$ and $R^2$ are H, $R^4$ is Br, $R^1$ is $OCF_3$ and wherein n and $R^5$ are as defined in one row of table A;

Table A106: Compounds of formula I, wherein each of $R^3$ and $R^2$ are H, $R^4$ is Br, $R^1$ is $OCHF_2$ and wherein n and $R^5$ are as defined in one row of table A;

Table A107: Compounds of formula I, wherein each of $R^3$ and $R^2$ are H, $R^4$ is Br, $R^1$ is $OCClF_2$ and wherein n and $R^5$ are as defined in one row of table A;

Table A108: Compounds of formula I, wherein each of $R^3$ and $R^2$ are H, $R^4$ is Br, $R^1$ is $OCF_2CHClF$ and wherein n and $R^5$ are as defined in one row of table A;

Table A109: Compounds of formula I, wherein each of $R^3$ and $R^2$ are H, $R^4$ is J, $R^1$ is $CH_3$ and wherein n and $R^5$ are as defined in one row of table A;

Table A110: Compounds of formula I, wherein each of $R^3$ and $R^2$ are H, $R^4$ is J, $R^1$ is $C_2H_5$ and wherein n and $R^5$ are as defined in one row of table A;

Table A111: Compounds of formula I, wherein each of $R^3$ and $R^2$ are H, $R^4$ is J, $R^1$ is $CF_3$ and wherein n and $R^5$ are as defined in one row of table A;

Table A112: Compounds of formula I, wherein each of $R^3$ and $R^2$ are H, $R^4$ is J, $R^1$ is $OCH_3$ and wherein n and $R^5$ are as defined in one row of table A;

Table A113: Compounds of formula I, wherein each of $R^3$ and $R^2$ are H, $R^4$ is J, $R^1$ is $OC_2H_5$ and wherein n and $R^5$ are as defined in one row of table A;

Table A114: Compounds of formula I, wherein each of $R^3$ and $R^2$ are H, $R^4$ is J, $R^1$ is $OCF_3$ and wherein n and $R^5$ are as defined in one row of table. A;

Table A115: Compounds of formula I, wherein each of $R^3$ and $R^2$ are H, $R^4$ is J, $R^1$ is $OCHF_2$ and wherein n and $R^5$ are as defined in one row of table A;

Table A116: Compounds of formula I, wherein each of $R^3$ and $R^2$ are H, $R^4$ is J, $R^1$ is $OCClF_2$ and wherein n and $R^5$ are as defined in one row of table A;

Table A117: Compounds of formula I, wherein each of $R^3$ and $R^2$ are H, $R^4$ is J, $R^1$ is $OCF_2CHClF$ and wherein n and $R^5$ are as defined in one row of table A;

Table A118: Compounds of formula I, wherein each of $R^4$ and $R^2$ are F, $R^3$ is H, $R^1$ is $CH_3$ and wherein n and $R^5$ are as defined in one row of table A;

Table A119: Compounds of formula I, wherein each of $R^4$ and $R^2$ are F, $R^3$ is H, $R^1$ is $C_2H_5$ and wherein n and $R^5$ are as defined in one row of table A;

Table A120: Compounds of formula I, wherein each of $R^4$ and $R^2$ are F, $R^3$ is H, $R^1$ is $CF_3$ and wherein n and $R^5$ are as defined in one row of table A;

Table A121: Compounds of formula I, wherein each of $R^4$ and $R^2$ are F, $R^3$ is H, $R^1$ is $OCH_3$ and wherein n and $R^5$ are as defined in one row of table A;

Table A122: Compounds of formula I, wherein each of $R^4$ and $R^2$ are F, $R^3$ is H, $R^1$ is $OC_2H_5$ and wherein n and $R^5$ are as defined in one row of table A;

Table A123: Compounds of formula I, wherein each of $R^4$ and $R^2$ are F, $R^3$ is H, $R^1$ is $OCF_3$ and wherein n and $R^5$ are as defined in one row of table A;

Table A124: Compounds of formula I, wherein each of $R^4$ and $R^2$ are F, $R^3$ is H, $R^1$ is $OCHF_2$ and wherein n and $R^5$ are as defined in one row of table A;

Table A125: Compounds of formula I, wherein each of $R^4$ and $R^2$ are F, $R^3$ is H, $R^1$ is $OCClF_2$ and wherein n and $R^5$ are as defined in one row of table A;

Table A126: Compounds of formula I, wherein each of $R^4$ and $R^2$ are F, $R^3$ is H, $R^1$ is $OCF_2CHClF$ and wherein n and $R^5$ are as defined in one row of table A;

Formula I is represented by the following two isomeric formulae:

TABLE A

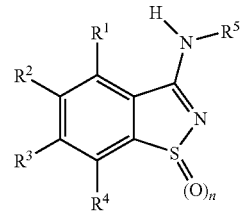

Formula Ia

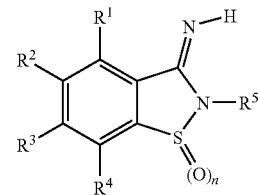

Formula Ib referring to formula I:

| No. | Isomeric formula I | $R^5$ |
|---|---|---|
| 1. | (Ia$_2$) | H |
| 2. | (Ia$_2$) | $CH_3$— |
| 3. | (Ia$_2$) | $CH_3CH_2$— |
| 4. | (Ia$_2$) | $CH_2$=CH— |
| 5. | (Ia$_2$) | $CH_3$—O—$CH_2$— |
| 6. | (Ia$_2$) | $ClCH_2$—$CH_2$— |
| 7. | (Ia$_2$) | $FCH_2$—$CH_2$— |
| 8. | (Ia$_2$) | $F_3C$—$CH_2$— |
| 9. | (Ia$_2$) | $Cl_3C$—$CH_2$— |
| 10. | (Ia$_2$) | $HOCH_2$—$CH_2$— |
| 11. | (Ia$_2$) | $CH_3$—O—$CH_2$—$CH_2$— |
| 12. | (Ia$_2$) | $(CH_3)_2CH$— |
| 13. | (Ia$_2$) | $CH_3CH_2CH_2$— |
| 14. | (Ia$_2$) | CN—$CH_2$— |
| 15. | (Ia$_2$) | CN—$CH_2$—$CH_2$ |
| 16. | (Ia$_2$) | $F_3C$—$CH_2$—$CH_2$— |
| 17. | (Ia$_2$) | $Cl_3C$—$CH_2$—$CH_2$— |
| 18. | (Ia$_2$) | $CH_3$—$CH_2$—$CH_2$—$CH_2$— |
| 19. | (Ia$_2$) | $CH_3$—$CH_2$—CH($CH_3$)— |
| 20. | (Ia$_2$) | $CH_3$—CH($CH_3$)—$CH_2$— |
| 21. | (Ia$_2$) | $CH_2$=C($CH_3$)—$CH_2$— |
| 22. | (Ia$_2$) | CH≡C—CH($CH_3$)— |
| 23. | (Ia$_2$) | CH≡CH—$CH_2$— |
| 24. | (Ia$_2$) | $(CH_3)_3C$— |
| 25. | (Ia$_2$) | HO |
| 26. | (Ia$_2$) | $CH_3O$— |
| 27. | (Ia$_2$) | $CH_3$—$CH_2$—O— |
| 28. | (Ia$_2$) | $(CH_3)_2$—$CH_2$—O |
| 29. | (Ia$_2$) | $CH_3$—$CH_2$—$CH_2$—O |
| 30. | (Ia$_2$) | $CH_2$=CH—$CH_2$—O— |
| 31. | (Ia$_2$) | $CH_2$=CH—$CH_2$— |
| 32. | (Ia$_2$) | CH≡C—$CH_2$—O— |
| 33. | (Ia$_2$) | $(CH_3)_3C$—O— |
| 34. | (Ia$_2$) | $(CH_3)_2$—$CH_2$—$CH_2$—O |
| 35. | (Ia$_2$) | $CH_3NH$— |
| 36. | (Ia$_2$) | $(CH_3)_2N$— |
| 37. | (Ia$_2$) | $C_2H_5NH$— |
| 38. | (Ia$_2$) | $(C_2H_5)_2N$— |
| 39. | (Ia$_2$) | $CH_3CONH$— |
| 40. | (Ia$_2$) | $CH_3CON(CH_3)$— |

TABLE A-continued

| | | |
|---|---|---|
| 41. | (Ia₂) | 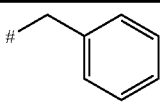 |
| 42. | (Ia₂) |  |
| 43. | (Ia₂) | 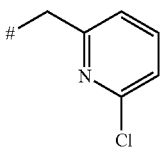 |
| 44. | (Ia₂) | 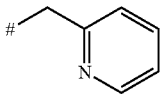 |
| 45. | (Ia₂) | 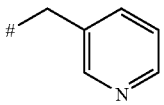 |
| 46. | (Ia₂) | 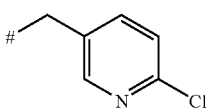 |
| 47. | (Ia₂) | 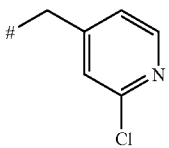 |
| 48. | (Ia₂) | 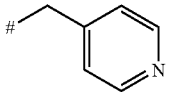 |
| 49. | 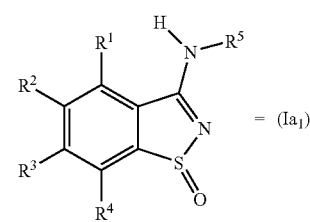 = (Ia₁) | H |
| 50. | (Ia₁) | $CH_3-$ |
| 51. | (Ia₁) | $CH_3CH_2-$ |
| 52. | (Ia₁) | $CH_2=CH-$ |
| 53. | (Ia₁) | $CH_3-O-CH_2-$ |
| 54. | (Ia₁) | $ClCH_2-CH_2-$ |
| 55. | (Ia₁) | $FCH_2-CH_2-$ |
| 56. | (Ia₁) | $F_3C-CH_2-$ |
| 57. | (Ia₁) | $Cl_3C-CH_2-$ |
| 58. | (Ia₁) | $HOCH_2-CH_2-$ |
| 59. | (Ia₁) | $CH_3-O-CH_2-CH_2-$ |
| 60. | (Ia₁) | $(CH_3)_2CH-$ |
| 61. | (Ia₁) | $CH_3CH_2CH_2-$ |
| 62. | (Ia₁) | $CN-CH_2-$ |
| 63. | (Ia₁) | $CN-CH_2-CH_2-$ |
| 64. | (Ia₁) | $F_3C-CH_2-CH_2-$ |
| 65. | (Ia₁) | $Cl_3C-CH_2-CH_2-$ |
| 66. | (Ia₁) | $CH_3-CH_2-CH_2-CH_2-$ |
| 67. | (Ia₁) | $CH_3-CH_2-CH(CH_3)-$ |
| 68. | (Ia₁) | $CH_3-CH(CH_3)-CH_2-$ |
| 69. | (Ia₁) | $CH_2=C(CH_3)-CH_2-$ |
| 70. | (Ia₁) | $CH\equiv C-CH(CH_3)-$ |
| 71. | (Ia₁) | $CH=CH-CH_2-$ |
| 72. | (Ia₁) | $(CH_3)_3C-$ |
| 73. | (Ia₁) | $HO$ |
| 74. | (Ia₁) | $CH_3O-$ |
| 75. | (Ia₁) | $CH_3-CH_2-O-$ |
| 76. | (Ia₁) | $(CH_3)_2-CH_2-O$ |
| 77. | (Ia₁) | $CH_3-CH_2-CH_2-O-$ |
| 78. | (Ia₁) | $CH_2=CH-CH_2-O-$ |
| 79. | (Ia₁) | $CH_2=CH-CH_2-$ |
| 80. | (Ia₁) | $CH\equiv C-CH_2-O-$ |
| 81. | (Ia₁) | $(CH_3)_3C-O-$ |
| 82. | (Ia₁) | $(CH_3)_2-CH_2-CH_2-O-$ |
| 83. | (Ia₁) | $CH_3NH-$ |
| 84. | (Ia₁) | $(CH_3)_2N-$ |
| 85. | (Ia₁) | $C_2H_5NH-$ |
| 86. | (Ia₁) | $(C_2H_5)_2N-$ |
| 87. | (Ia₁) | $CH_3CONH-$ |
| 88. | (Ia₁) | $CH_3CON(CH_3)-$ |
| 89. | (Ia₁) | 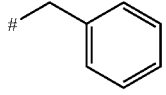 |
| 90. | (Ia₁) |  |
| 91. | (Ia₁) | 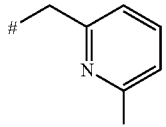 |
| 92. | (Ia₁) | 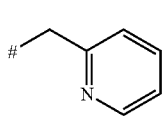 |
| 93. | (Ia₁) | 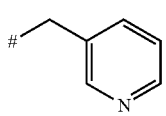 |
| 94. | (Ia₁) | 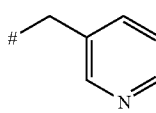 |
| 95. | (Ia₁) | 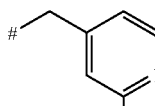 |
| 96. | (Ia₁) | 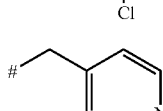 |
| 97. | 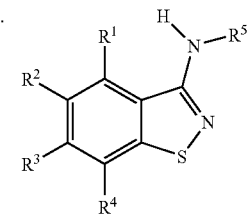 = (Ia) | $CH_3-$ |
| 98. | (Ia) | $CH_3CH_2-$ |
| 99. | (Ia) | $CH_2=CH-$ |

TABLE A-continued

| | | |
|---|---|---|
| 100. | (Ia) | CH$_3$—O—CH$_2$— |
| 101. | (Ia) | ClCH$_2$—CH$_2$— |
| 102. | (Ia) | FCH$_2$—CH$_2$— |
| 103. | (Ia) | F$_3$C—CH$_2$— |
| 104. | (Ia) | Cl$_3$C—CH$_2$— |
| 105. | (Ia) | HOCH$_2$—CH$_2$— |
| 106. | (Ia) | CH$_3$—O—CH$_2$—CH$_2$— |
| 107. | (Ia) | (CH$_3$)$_2$CH— |
| 108. | (Ia) | CH$_3$CH$_2$CH$_2$— |
| 109. | (Ia) | CN—CH$_2$— |
| 110. | (Ia) | CN—CH$_2$—CH$_2$ |
| 111. | (Ia) | F$_3$C—CH$_2$—CH$_2$— |
| 112. | (Ia) | Cl$_3$C—CH$_2$—CH$_2$— |
| 113. | (Ia) | CH$_3$—CH$_2$—CH$_2$—CH$_2$— |
| 114. | (Ia) | CH$_3$—CH$_2$—CH(CH$_3$)— |
| 115. | (Ia) | CH$_3$—CH(CH$_3$)—CH$_2$— |
| 116. | (Ia) | CH$_2$=C(CH$_3$)—CH$_2$— |
| 117. | (Ia) | CH≡C—CH(CH$_3$)— |
| 118. | (Ia) | CH≡C—CH$_2$— |
| 119. | (Ia) | (CH$_3$)$_3$C— |
| 120. | (Ia) | HO |
| 121. | (Ia) | CH$_3$O— |
| 122. | (Ia) | CH$_3$—CH$_2$—O— |
| 123. | (Ia) | (CH$_3$)$_2$—CH$_2$—O |
| 124. | (Ia) | CH$_3$—CH$_2$—CH$_2$—O |
| 125. | (Ia) | CH$_2$=CH—CH$_2$—O— |
| 126. | (Ia) | CH$_2$=CH—CH$_2$— |
| 127. | (Ia) | CH≡C—CH$_2$—O— |
| 128. | (Ia) | (CH$_3$)$_3$C—O— |
| 129. | (Ia) | (CH$_3$)$_2$—CH$_2$—CH$_2$—O |
| 130. | (Ia) | CH$_3$NH— |
| 131. | (Ia) | (CH$_3$)$_2$N— |
| 132. | (Ia) | C$_2$H$_5$NH— |
| 133. | (Ia) | (C$_2$H$_5$)$_2$N— |
| 134. | (Ia) | CH$_3$CONH— |
| 135. | (Ia) | CH$_3$CON(CH$_3$)— |
| 136. | (Ia) | 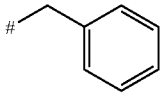 |
| 137. | (Ia) |  |
| 138. | (Ia) | 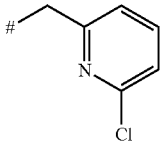 |
| 139. | (Ia) | 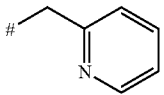 |
| 140. | (Ia) | 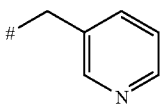 |
| 141. | (Ia) | 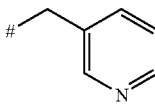 |
| 142. | (Ia) | 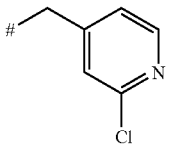 |
| 143. | (Ia) | 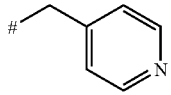 |
| 144. | 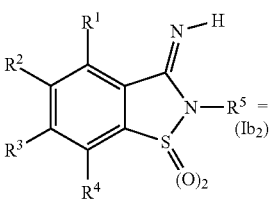 (Ib$_2$) | CH$_3$— |
| 145. | (Ib$_2$) | CH$_3$CH$_2$— |
| 146. | (Ib$_2$) | CH$_2$=CH— |
| 147. | (Ib$_2$) | CH$_2$=CH—CH$_2$— |
| 148. | (Ib$_2$) | CH≡CH—CH$_2$— |
| 149. | (Ib$_2$) | CH$_3$—O—CH$_2$— |
| 150. | (Ib$_2$) | ClCH$_2$—CH$_2$— |
| 151. | (Ib$_2$) | FCH$_2$—CH$_2$— |
| 152. | (Ib$_2$) | F$_3$C—CH$_2$— |
| 153. | (Ib$_2$) | Cl$_3$C—CH$_2$— |
| 154. | (Ib$_2$) | HOCH$_2$—CH$_2$— |
| 155. | (Ib$_2$) | CH$_3$—O—CH$_2$—CH$_2$— |
| 156. | (Ib$_2$) | (CH$_3$)$_2$CH— |
| 157. | (Ib$_2$) | CH$_3$CH$_2$CH$_2$— |
| 158. | (Ib$_2$) | CN—CH$_2$— |
| 159. | (Ib$_2$) | CN—CH$_2$—CH$_2$ |
| 160. | (Ib$_2$) | F$_3$C—CH$_2$—CH$_2$— |
| 161. | (Ib$_2$) | Cl$_3$C—CH$_2$—CH$_2$— |
| 162. | (Ib$_2$) | CH$_3$—CH$_2$—CH$_2$—CH$_2$— |
| 163. | (Ib$_2$) | CH$_3$—CH$_2$—CH(CH$_3$)— |
| 164. | (Ib$_2$) | CH$_3$—CH(CH$_3$)—CH$_2$— |
| 165. | (Ib$_2$) | CH$_2$=C(CH$_3$)—CH$_2$— |
| 166. | (Ib$_2$) | CH≡C—CH(CH$_3$)— |
| 167. | (Ib$_2$) | (CH$_3$)$_3$C— |
| 168. | (Ib$_2$) | 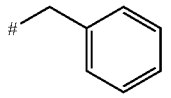 |
| 169. | (Ib$_2$) |  |
| 170. | (Ib$_2$) | 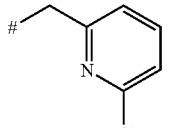 |
| 171. | (Ib$_2$) | 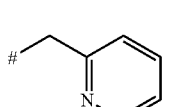 |
| 172. | (Ib$_2$) | 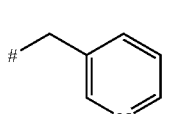 |
| 173. | (Ib$_2$) | 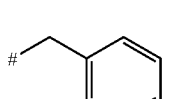 |

TABLE A-continued 174. (Ib$_2$) 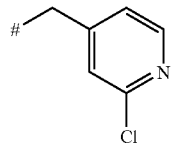

175. (Ib$_2$) 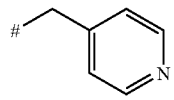

wherein, # in formulae defining R$^5$ denote the bond to formula I;

Pests

The compounds of the formula I, and their salts are in particular suitable for efficiently controlling arthropodal pests such as arachnids, myriapedes and insects as well as nematodes.

In particular, they are suitable for controlling insect pests, such as insects from the order of Lepidoptera: for example *Agrotis ypsllon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera eridania, Spodoptera frugiperda, Spodoptera littoralis, Spodoptera litura, Thaumatopoea pityocampa, Tortrix viridana, Trichoplusia ni* and *Zeiraphera canadensis*, Coleoptera (beetles), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longkornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bllineata, Lema melanopus, Leptinotarsa decemlineata, Limonius californicus, Lissorhoptrus oryzophllus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga* sp., *Phyllopertha horticola, Phyllotreta nemorum, Phyllotreta striolata, Popillia japonica, Sitona lineatus* and *Sitophllus granaria*, Diptera, for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca autumnalis, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa*, Thysanoptera (thrips), e.g. *Dichromothrips* spp., *Frankliniella fusca, Frankliniella occidentalis, Frankliniella tritici, Scirtothrips citri, Thrips oryzae, Thrips palmi* and *Thrips tabaci*, Hymenoptera, e.g. *Athalia rosae, Atta cephalotes, Atta sexdens, Atta texana, Hoplocampa minuta, Hoplocampa testudinea, Lasius niger, Monomorium pharaonis, Solenopsis geminata* and *Solenopsis invicta*, Heteroptera, e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor*, Homoptera (in particular aphids), e.g. *Acyrthosibhon onobrychis, Adelges laricis, Aphidula nasturtii, Aphis craccivora, Aphis fabae, Aphis forbesi Aphis pomi, Aphis gossypii, Aphis grossulariae, Aphis schneideri, Aphis spiraecola, Aphis sambuci, Acyrthosiphon pisum, Aulacorthum solani, Bemisa tabaci, Bemisa argentifolii, Brachycaudus cardui, Brachycaudus helichrysi, Brachycaudus persicae, Brachycaudus prunicola, Brevkoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalon/cus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand*, and *Viteus vitifolii*

Isoptera(termites), e.g. *Calotermes flavkollis, Leucotermes fiavipes, Reticulitermes grassei, Reticulitermes lucifugus, Reticulitermes santonensis* and *Termes natalensis*, Orthoptera, e.g. *Acheta domestica, Blatta orientalis, Blattella germanica, Forfkula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus*, and Collembola (springtails), e.g. *Onychiurus* ssp.

They are also suitable for controlling Nematodes: plant parasitic nematodes such as root knot nematodes, *Meloidogyne hapla*, *Meloidogyne incognita*, *Meloidogyne javanica*, and other *Meloidogyne* species; cyst-forming nematodes, *Globodera rostochiensis* and other *Globodera* species; *Heterodera avenae*, *Heterodera glycines*, *Heterodera schachtii*, *Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophllus* and other *Bursaphelenchus* species; Ring nematodes, *Criconema* species, *Criconemella* species, *Criconemoides* species, *Mesocriconema* species; Stem and bulb nematodes, *Ditylenchus destructor*, *Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Lesion nematodes, *Pratylenchus neglectus*, *Pratylenchus penetrans*, *Pratylenchus curvitatus*, *Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni*, *Tylenchorhynchus dubius* and other *Tylenchorhynchus* species; Citrus nematodes, *Tylenchulus* species; Dagger nematodes, *Xiphinema* species; and other plant parasitic nematode species.

The compounds of the formula I and their salts are also useful for controlling arachnids (Arachnoidea), such as acarians (Acarina), e.g. of the families Argasidae, Ixodidae and Sarcoptidae, such as *Amblyomma americanum*, *Amblyomma variegatum*, *Argas persicus*, *Boophilus annulatus*, *Boophilus decoloratus*, *Boophilus microplus*, *Dermacentor silvarum*, *Hyalomma truncatum*, *Ixodes ricinus*, *Ixodes rubicundus*, *Ornithodorus moubata*, *Otobius megnini*, *Dermanyssus gallinae*, *Psoroptes ovis*, *Rhipicephalus appendiculatus*, *Rhipicephalus evertsi*, *Sarcoptes scabiei*, and *Eriophyidae* spp. such as *Aculus schlechtendali*, *Phyllocoptrata oleivora* and *Eriophyes sheldoni*; *Tarsonemidae* spp. such as *Phytonemus pallidus* and *Polyphagotarsonemus latus*; *Tenuipalpidae* spp. such as *Brevipalpus phoenicis*; *Tetranychidae* spp. such as *Tetranychus cinnabarinus*, *Tetranychus kanzawai*, *Tetranychus pacificus*, *Tetranychus telarius* and *Tetranychus urticae*, *Panonychus ulmi*, *Panonychus citri*, and *oligonychus pratensis*.

Compounds of the formula I are particularly useful for controlling insects, preferably sucking or piercing insects such as insects from the genera *Thysanoptera*, *Hymenoptera*, *Orthoptera* and *Homptera*, in particular the following species:

Thysanoptera (thrips): *Frankliniella fusca*, *Frankliniella occidentalis*, *Frankliniella tritici*, *Scirtothrips citri*, *Thrips oryzae*, *Thrips palmi* and *Thrips tabaci*, Hymenoptera: *Athalia rosae*, *Atta cephalotes*, *Atta sexdens*, *Atta texana*, *Hoplocampa minuta*, *Hoplocampa testudinea*, *Monomorium pharaonis*, *Solenopsis geminata* and *Solenopsis invicta*, Orthoptera: *Acheta domestica*, *Blatta orientalis*, *Blattella germanica*, *Forficula auricularia*, *Gryllotalpa gryllotalpa*, *Locusta migratoria*, *Melanoplus bivittatus*, *Melanoplus femur-rubrum*, *Melanoplus mexicanus*, *Melanoplus sanguinipes*, *Melanoplus spretus*, *Nomadacris septemfasciata*, *Periplaneta americana*, *Schistocerca americana*, *Schistocerca peregrina*, *Stauronotus maroccanus* and *Tachycines asynamorus*;

Homoptera, in particular aphids: *Acyrthosiphon onobrychis*, *Adelges laricis*, *Aphidula nasturtii*, *Aphis fabae*, *Aphis forbesi*, *Aphis pomi*, *Aphis gossypii*, *Aphis grossulariae*, *Aphis schneideri*, *Aphis spiraecola*, *Aphis sambuci*, *Acyrthosiphon pisum*, *Aulacorthum solani*, *Brachycaudus cardui*, *Brachycaudus helichrysi*, *Brachycaudus persicae*, *Brachycaudus prunicola*, *Brevicoryne brassicae*, *Capitophorus horni*, *Cerosipha gossypii*, *Chaetosiphon fragaefolii*, *Cryptomyzus ribis*, *Dreyfusia nordmannianae*, *Dreyfusia piceae*, *Dysaphis radicola*, *Dysaulacorthum pseudosolani*, *Dysaphis plantaginea*, *Dysaphis pyri*, *Empoasca fabae*, *Hyalopterus pruni*, *Hyperomyzus lactucae*, *Macrosiphum avenae*, *Macrosiphum euphorbiae*, *Macrosiphon rosae*, *Megoura viciae*, *Melanaphis pyrarius*, *Metopolophium dirhodum*, *Myzodes persicae*, *Myzus ascalonicus*, *Myzus cerasi*, *Myzus varians*, *Nasonovia Nilaparvata lugens*, *Pemphigus bursarius*, *Perkinsiella saccharicida*, *Phorodon humuli*, *Psylla mali*, *Psylla piri*, *Rhopalomyzus ascalonicus*, *Rhopalosiphum maidis*, *Rhopalosiphum padi*, *Rhopalosiphum insertum*, *Sappaphis mala*, *Sappaphis mali*, *Schizaphis graminum*, *Schizoneura lanuginosa*, *Sitobion avenae*, *Trialeurodes vaporariorum*, *Toxoptera aurantiiand*, and *Viteus vitifolii*;

Compounds of the formula I are particularly useful for controlling insects of the orders *Homoptera* and Thysanoptera and more preferably for controlling aphids.

Formulations

For use in a method according to the present invention, the compounds I can be converted into the customary formulations, e.g. solutions, emulsions, suspensions, dusts, powders, pastes, granules and directly sprayable solutions. The use form depends on the particular purpose and application method. Formulations and application methods are chosen to ensure in each case a fine and uniform distribution of the compound of the formula I according to the present invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, anti-foaming agents, anti-freezing agents, for seed treatment formulation also optionally colorants and/or binders and/or gelling agents.

Solvents/carriers, which are suitable, are e.g.:
solvents such as water, aromatic solvents (for example Solvesso products, xylene and the like), paraffins (for example mineral fractions), alcohols (for example methanol, butanol, pentanol, benzyl alcohol), ketones (for example cyclohexanone, gamma-butyrolactone), pyrrolidones (N-methyl-pyrrolidone (NMP), N-octylpyrrolidone NOP), acetates (glycol diacetate), alkyl lactates, lactones such as g-butyrolactone, glycols, fatty acid dimethylamides, fatty acids and fatty acid esters, triglycerides, oils of vegetable or animal origin and modified oils such as alkylated plant oils. In principle, solvent mixtures may also be used.

carriers such as ground natural minerals and ground synthetic minerals, such as silica gels, finely divided silicic acid, silicates, talc, kaolin, attaclay, limestone, lime, chalk, bole, loess, clay, dolomite, diatomaceous earth, calcium sulfate and magnesium sulfate, magnesium oxide, ground synthetic materials, fertilizers, such as, for example, ammonium sulfate, ammonium phosphate, ammonium nitrate, ureas and products of vegetable origin, such as cereal meal, tree bark meal, wood meal and nutshell meal, cellulose powders and other solid carriers.

Suitable emulsifiers are nonionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, Also anti-freezing agents such as glycerin, ethylene glycol, propylene glycol and bactericides such as can be added to the formulation.

Suitable antifoaming agents are for example antifoaming agents based on silicon or magnesium stearate.

Suitable preservatives are for example dichlorophen and benzyl alcohol hemiformal Suitable thickeners are compounds which confer a pseudoplastic flow behavior to the formulation, i.e. high viscosity at rest and low viscosity in the agitated stage. Mention may be made, in this context, for example, of commercial thickeners based on polysaccharides, such as Xanthan Gum® (Kelzan® from Kelco), Rhodopol®23 (Rhone Poulenc) or Veegum® (from R.T. Vanderbilt), or organic phyllosilicates, such as Attaclay® (from Engelhardt). Antifoam agents suitable for the dispersions according to the invention are, for example, silicone emulsions (such as, for example, Silikon® SRE, Wacker or Rhodorsil® from Rhodia), long-chain alcohols, fatty acids, organofluorine compounds and mixtures thereof. Biocides can be added to stabilize the compositions according to the invention against attack by microorganisms. Suitable biocides are, for example, based on isothiazolones such as the compounds marketed under the trademarks Proxel® from Avecia (or Arch) or Acticide® RS from Thor Chemie and Kathon® MK from Rohm & Haas. Suitable antifreeze agents are organic polyols, for example ethylene glycol, propylene glycol or glycerol. These are usually employed in amounts of not more than 10% by weight, based on the total weight of the active compound composition. If appropriate, the active compound compositions according to the invention may comprise 1 to 5% by weight of buffer, based on the total amount of the formulation prepared, to regulate the pH, the amount and type of the buffer used depending on the chemical properties of the active compound or the active compounds. Examples of buffers are alkali metal salts of weak inorganic or organic acids, such as, for example, phosphoric acid, boronic acid, acetic acid, propionic acid, citric acid, fumaric acid, tartaric acid, oxalic acid and succinic acid.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for spreading and dusts can be prepared by mixing or concomitantly grinding the active substances with a solid carrier.

Granules, for example coated granules, impregnated granules and homogeneous granules, can be prepared by binding the active ingredients to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active ingredient. The active ingredients are employed in a purity of from 90% to 100%, preferably 95% to 100% (according to NMR spectrum).

For seed treatment purposes, respective formulations can be diluted 2-10 fold leading to concentrations in the ready to use preparations of 0.01 to 60% by weight active compound by weight, preferably 0.1 to 40% by weight.

The compound of formula I can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compounds according to the invention.

The following are examples of formulations:

1. Products for dilution with water. For seed treatment purposes, such products may be applied to the seed diluted or undiluted.

A) Water-Soluble Concentrates (SL, Ls)

10 parts by weight of the active compound is dissolved in 90 parts by weight of water or a water-soluble solvent. As an alternative, wetters or other auxiliaries are added. The active compound dissolves upon dilution with water, whereby a formulation with 10% (w/w) of active compound is obtained.

B) Dispersible Concentrates (DC)

20 parts by weight of the active compound is dissolved in 70 parts by weight of cyclohexanone with addition of 10 parts by weight of a dispersant, for example polyvinylpyrrolidone.

Dilution with water gives a dispersion, whereby a formulation with 20% (w/w) of active compounds is obtained.

C) Emulsifiable Concentrates (EC)

15 parts by weight of the active compounds is dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compounds is obtained.

D) Emulsions (EW, EO, ES)

25 parts by weight of the active compound is dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound is obtained.

E) Suspensions (SC, OD, FS)

In an agitated ball mill, 20 parts by weight of the active compound is comminuted with addition of 10 parts by weight of dispersants, wetters and 70 parts by weight of water or of an organic solvent to give a fine active compound suspension. Dilution with water gives a stable suspension of the active compound, whereby a formulation with 20% (w/w) of active compound is obtained.

F) Water-Dispersible Granules and Water-Soluble Granules (WG, SG)

50 parts by weight of the active compound is ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound, whereby a formulation with 50% (w/w) of active compound is obtained.

G) Water-Dispersible Powders and Water-Soluble Powders (WP, SP, SS, WS)

75 parts by weight of the active compound are ground in a rotor-stator mill with addition of 25 parts by weight of dispersants, wetters and silica gel. Dilution with water gives a stable dispersion or solution of the active compound, whereby a formulation with 75% (w/w) of active compound is obtained.

H) Gel-Formulation (GF)

In an agitated ball mill, 20 parts by weight of the active compound is comminuted with addition of 10 parts by weight of dispersants, 1 part by weight of a gelling agent wetters and 70 parts by weight of water or of an organic solvent to give a fine active compound suspension. Dilution with water gives a stable suspension of the active compound, whereby a formulation with 20% (w/w) of active compound is obtained.

2. Products to be applied undiluted for foliar applications. For seed treatment purposes, such products may be applied to the seed diluted or undiluted.

I) Dustable Powders (DP, DS)

5 parts by weight of the active compound are ground finely and mixed intimately with 95 parts by weight of finely divided kaolin. This gives a dustable product having 5% (w/w) of active compound.

J) Granules (GR, FG, GG, MG)

0.5 part by weight of the active compound is ground finely and associated with 95.5 parts by weight of carriers, whereby a formulation with 0.5% (w/w) of active compound is obtained. Current methods are extrusion, spray-drying or the fluidized bed. This gives granules to be applied undiluted for foliar use.

K) ULV Solutions (UL)

10 parts by weight of the active compound is dissolved in 90 parts by weight of an organic solvent, for example xylene. This gives a product having 10% (w/w) of active compound, which is applied undiluted for foliar use.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within relatively wide ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even to apply the active ingredient without additives.

In the method of this invention compounds I may be applied with other active ingredients, for example with other pesticides, insecticides, herbicides, fertilizers such as ammonium nitrate, urea, potash, and superphosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

The following list M of pesticides together with which the compounds according to the invention can be used and with which potential synergistic effects might be produced, is intended to illustrate the possible combinations, but not to impose any limitation:

M.1. Organo(thio)phosphates: acephate, azamethiphos, azinphos-ethyl, azinphosmethyl, chlorethoxyfos, chlorfenvinphos, chlormephos, chlorpyrifos, chlorpyrifosmethyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion;

M.2. Carbamates: aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb, triazamate;

M.3. Pyrethroids: acrinathrin, allethrin, d-cis-trans allethrin, d-trans allethrin, bifenthrin, bioallethrin, bioallethrin S-cyclopentenyl, bioresmethrin, cycloprothrin, cyfluthrin, beta-, yfluthrin, cyhalothrin, lambda-cyhalothrin, gamma-cyhalothrin, cypermethrin, alphacypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, permethrin, phenothrin, prallethrin, resmethrin, RU 15525, silafluofen, tefluthrin, tetramethrin, tralomethrin, transfluthrin, ZXI 8901;

M.4. Juvenile hormone mimics: hydroprene, kinoprene, methoprene, fenoxycarb, pyriproxyfen;

M.5. Nicotinic receptor agonists/antagonists compounds: acetamiprid, bensultap, cartap hydrochloride, clothianidin, dinotefuran, imidacloprid, thiamethoxam, nitenpyram, nicotine, spinosad (allosteric agonist), thiacloprid, thiocyclam, thiosultap-sodium, the thiazol compound AKD-1022 of formula ($M^{5.1}$)

($M^{5.1}$)

M.6. GABA gated chloride channel antagonist compounds: chlordane, endosulfan, gamma-HCH (lindane); acetoprole, ethiprole, fipronil, pyrafluprole, pyriprole, vaniliprole, the phenylpyrazole compound of formula $M^{6.1}$ ($M^{6.1}$)

M.7. Chloride channel activators: abamectin, emamectin benzoate, milbemectin, lepimectin;

M.8. METI I compounds: fenazaquin, fenpyroximate, pyrimidifen, pyridaben, tebufenpyrad, tolfenpyrad, flufenerim, rotenone;

M.9. METI II and III compounds: acequinocyl, fluacyprim, hydramethylnon;

M.10. Uncouplers of oxidative phosphorylation: chlorfenapyr, DNOC;

M.11. Inhibitors of oxidative phosphorylation: azocyclotin, cyhexatin, diafenthiuron, fenbutatin oxide, propargite, tetradifon;

M.12. Moulting disruptors: cyromazine, chromafenozide, halofenozide, methoxyfenozide, tebufenozide;

M.13. Synergists: piperonyl butoxide, tribufos;

M.14. Sodium channel blocker compounds: indoxacarb, metaflumizone;

M.15. Fumigants: methyl bromide, chloropicrin sulfuryl fluoride;

M.16. Selective feeding blockers: crylotie, pymetrozine, flonicamid;

M.17. Mite growth inhibitors: clofentezine, hexythiazox, etoxazole;

M.18: Chitin synthesis inhibitors: buprofezin, bistrifluoron, chlorfluazuron, diflubenzuron, flucycloxuron, flufenoxuron, hexaflumuron, lufenuron, novaluron, noviflumuron, teflubenzuron, triflumuron;

M.19. Lipid biosynthesis inhibitors: spirodiclofen, spiromesifen, spirotetramat;

M.20. octapaminergic agonists: amitraz;

M.21. ryanodine receptor modulators: flubendiamide;

M.22. Various: aluminium phosphide, amidoflumet, benclothiaz, benzoximate, bifenazate, borax, bromopropylate, cyanide, cyenopyrafen, cyflumetofen, chinomethionate, dicofol, fluoroacetate, phosphine, pyridalyl, pyrifluquinazon, sulfur, tartar emetic;

M.23. N-R'-2,2-dihalo-1-R''cyclo-propanecarboxamide-2-(2,6-dichloro-α,α,α-tri-fluorop-tolyl)hydrazone or N-R'-2,2-di(R''')propionamide-2-(2,6-dichloro-α,α,α-trifluoroptolyl)-hydrazone, wherein R' is methyl or ethyl, halo is chloro or bromo, R'' is hydrogen or methyl and R''' is methyl or ethyl;

M.24. Anthranilamides: chloranthraniliprole, the compound of formula $M^{24.1}$ ($M^{24.1}$)

M.25. Malononitrile compounds: $CF_3(CH_2)_2C(CN)_2CH_2(CF_2)_3CF_2H$, $CF_3(CH_2)_2C(CN)_2CH_2(CF_2)_5CF_2H$, $CF_3(CH_2)_2C(CN)_2(CH_2)_2C(CF_3)_2F$, $CF_3(CH_2)_2C(CN)_2(CH_2)_2(CF_2)_3CF_3$, $CF_2H(CF_2)_3CH_2C(CN)_2CH_2(CF_2)_3CF_2H$, $CF_3(CH_2)_2C(CN)_2CH_2(CF_2)_3CF_3$, $CF_3(CF_2)_2CH_2C(CN)_2CH_2(CF_2)_3CF_2H$, and $CF_3CF_2CH_2C(CN)_2CH_2(CF_2)_3CF_2H$;

M.26. Microbial disruptors: *Bacillus thuringiensis* subsp. *Israelensi*, *Bacillus sphaericus*, *Bacillus thuringiensis* subsp. *Aizawai*, *Bacillus thuringiensis* subsp. *Kurstaki*, *Bacillus thuringiensis* subsp. *Tenebrionis*;

The commercially available compounds of the group M may be found in The Pesticide Manual, 13$^{th}$ Edition, British Crop Protection Council (2003) among other publications.

Thioamides of formula $M^{6.1}$ and their preparation have been described in WO 98/28279. Lepimectin is known from Agro Project, PJB Publications Ltd, November 2004. Benclothiaz and its preparation have been described in EP-A1 454621. Methidathion and Paraoxon and their preparation have been described in Farm Chemicals Handbook, Volume 88, Meister Publishing Company, 2001. Acetoprole and its preparation have been described in WO 98/28277. Metaflumizone and its preparation have been described in EP-A1 462 456. Flupyrazofos has been described in Pesticide Science 54, 1988, p. 237-243 and in U.S. Pat. No. 4,822,779. Pyrafluprole and its preparation have been described in JP 2002193709 and in WO 01/00614. Pyriprole and its preparation have been described in WO 98/45274 and in U.S. Pat. No. 6,335,357. Amidoflumet and its preparation have been described in U.S. Pat. No. 6,221,890 and in JP 21010907. Flufenerim and its preparation have been described in WO 03/007717 and in WO 03/007718. Preparation methods for neonicotionids similar to AKD-1022 ($M^{5.1}$) have been desscribed by Zhang, A. et al. in J. Neurochemistry, 75(3), 2000. Chloranthraniliprole and anthranilamide derivatives in analogy of formula $M^{24.1}$ and their preparation have been described in WO 01/70671; WO 02/48137; WO 03/24222, WO 03/15518, WO 04/67528; WO 04/33468 and WO 05/118552. Cyflumetofen and its preparation have been described in WO 04/080180. The aminoquinazolinone compound pyrifluquinazon has been described in EPA 109 7932. The malononitrile compounds $CF_3(CH_2)_2C(CN)_2CH_2(CF_2)_3CF_2H$, $CF_3(CH_2)_2C(CN)_2CH_2(CF_2)_5CF_2H$, $CF_3(CH_2)_2C(CN)_2(CH_2)_2C(CF_3)_2F$, $CF_3(CH_2)_2C(CN)_2(CH_2)_2(CF_2)_3CF_3$, $CF_2H(CF_2)_3CH_2C(CN)_2CH_2(CF_2)_3CF_2H$, $CF_3(CH_2)_2C(CN)_2CH_2(CF_2)_3CF_3$, $CF_3(CF_2)_2CH_2C(CN)_2CH_2(CF_2)_3CF_2H$, and $CF_3CF_2CH_2C(CN)_2CH_2(CF_2)_3CF_2H$ have been described in WO 05/63694.

Fungicidal mixing partners are those selected from the group F consisting of

F.1 acylalanines such as benalaxyl, metalaxyl, ofurace, oxadixyl;

F.2 amine derivatives such as aldimorph, dodine, dodemorph, fenpropimorph, fenpropidin, guazatine, iminoctadine, spiroxamin, tridemorph;

F.3 anilinopyrimidines such as pyrimethanil, mepanipyrim or cyrodinyl;

F.4 antibiotics such as cycloheximid, griseofulvin, kasugamycin, natamycin, polyoxin or streptomycin;

F.5 azoles such as bitertanol, bromoconazole, cyproconazole, difenoconazole, dinitroconazole, epoxiconazole, fenbuconazole, fluquiconazole, flusilazole, hexaconazole, imazalil, metconazole, myclobutanil, penconazole, propiconazole, prochloraz, prothioconazole, tebuconazole, triadimefon, triadimenol, triflumizol, triticonazole, flutriafol;

F.6 dicarboximides such as iprodion, myclozolin, procymidon, vinclozolin;

F.7 dithiocarbamates such as ferbam, nabam, maneb, mancozeb, metam, metiram, propineb, polycarbamate, thiram, ziram, zineb;

F.8 heterocyclic compounds such as anilazine, benomyl, boscalid, carbendazim, carboxin, oxycarboxin, cyazofamid, dazomet, dithianon, famoxadon, fenamidon, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamid, thiophanate-methyl, tiadinil, tricyclazole, triforine;

F.9 copper fungicides such as Bordeaux mixture, copper acetate, copper oxychloride, basic copper sulfate;

F.10 nitrophenyl derivatives such as binapacryl, dinocap, dinobuton, nitrophthalisopropyl;

F.11 phenylpyrroles such as fenpiclonil or fludioxonil;

F.12 strobilurins such as azoxystrobin, dimoxystrobin, fluoxastrobin, kresoxim-methyl, metominostrobin, orysastrobin, picoxystrobin or trifloxystrobin;

F.13 sulfenic acid derivatives such as captafol, captan, dichiofluanid, folpet, tolylfluanid;

F.14 cinnemamides and analogs such as dimethomorph, flumetover or flumorph;

F.15 sulfur, and other fungicides such as acibenzolar-S-methyl, benthiavalicarb, carpropamid, chlorothalonil, cyflufenamid, cymoxanil, dazomet, diclomezin, diclocymet, diethofencarb, edifenphos, ethaboxam, fenhexamid, fentinacetate, fenoxanil, ferimzone, fluazinam, fosetyl, fosetyl-aluminum, iprovalicarb, hexachlorobenzene, metrafenon, pencycuron, propamocarb, phthalide, toloclofos-methyl, quintozene, zoxamid.

Applications

The animal pest, i.e. the insects, arachnids and nematodes, the plant, soil or water in which the plant is growing can be contacted with the present compound(s) I or composition(s) containing them by any application method known in the art. As such, "contacting" includes both direct contact (applying the compounds/compositions directly on the animal pest or plant—typically to the foliage, stem or roots of the plant) and indirect contact (applying the compounds/compositions to the locus of the animal pest or plant).

The compounds of formula I or the pesticidal compositions comprising them may be used to protect growing plants and crops from attack or infestation by animal pests, especially insects, acaridae or arachnids by contacting the plant/crop with a pesticidally effective amount of compounds of formula I. The term "crop" refers both to growing and harvested crops.

Moreover, animal pests may be controlled by contacting the target pest, its food supply, habitat, breeding ground or its locus with a pesticidally effective amount of compounds of formula I. As such, the application may be carried out before or after the infection of the locus, growing crops, or harvested crops by the pest.

The compounds of the invention can also be applied preventively to places at which occurrence of the pests is expected.

The compounds of formula I may be also used to protect growing plants from attack or infestation by pests by contacting the plant with a pesticidally effective amount of compounds of formula I. As such, "contacting" includes both direct contact (applying the compounds/compositions directly on the pest and/or plant—typically to the foliage, stem or roots of the plant) and indirect contact (applying the compounds/compositions to the locus of the pest and/or plant).

"Locus" means a habitat, breeding ground, plant, seed, soil, area, material or environment in which a pest or parasite is growing or may grow.

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment or of application to the pests dwelling place or nest, the quantity of active ingredient ranges from 0.0001 to 500 g per 100 $m^2$, preferably from 0.001 to 20 g per 100 $m^2$.

Customary application rates in the protection of materials are, for example, from 0.01 g to 1000 g of active compound per $m^2$ treated material, desirably from 0.1 g to 50 g per $m^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in treating crop plants, the rate of application of the active ingredients of this invention may be in the range of 0.1 g to 4000 g per hectare, desirably from 25 g to 600 g per hectare, more desirably from 50 g to 500 g per hectare.

The compounds of formula I are effective through both contact (via soil, glass, wall, bed net, carpet, plant parts or animal parts), and ingestion (bait, or plant part).

The compounds of the invention may also be applied against non-crop insect pests, such as ants, termites, wasps, flies, mosquitos, crickets, or cockroaches. For use against said non-crop pests, compounds of formula I are preferably used in a bait cornposition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics.

The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

For use in bait compositions, the typical content of active ingredient is from 0.001 weight % to 15 weight %, desirably from 0.001 weight % to 5% weight % of active compound.

Formulations of compounds of formula I as aerosols (e.g in spray cans), oil sprays or pump sprays are highly suitable for the non-professional user for controlling pests such as flies, fleas, ticks, mosquitos or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulfoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds of formula I and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formula I and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-Diethyl-meta-toluamide (DEET), N,N-diethylphenylacetamide (DEPA), 1-(3-cyclohexan-1-yl-carbonyl)-2-methylpiperine, (2-hydroxymethyl-cyclohexyl)acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and di-ethylenically unsaturated hydrocarbons, such as styrene, and aliphatic diens, such as butadiene.

The impregnation of curtains and bednets is done in general by dipping the textile material into emulsions or dispersions of the insecticide or spraying them onto the nets.

The compounds of formula I and its compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of formula I are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

Seed Treatment

The compounds of formula I are also suitable for the treatment of seeds in order to protect the seed from insect pest, in particular from soil-living insect pests and the resulting plant's roots and shoots against soil pests and foliar insects.

The compounds of formula I are particularly useful for the protection of the seed from soil pests and the resulting plant's roots and shoots against soil pests and foliar insects. The protection of the resulting plant's roots and shoots is preferred. More preferred is the protection of resulting plant's shoots from piercing and sucking insects, wherein the protection from aphids is most preferred.

The present invention therefore comprises a method for the protection of seeds from insects, in particular from soil insects and of the seedlings' roots and shoots from insects, in particular from soil and foliar insects, said method comprising contacting the seeds before sowing and/or after pregermination with a compound of the general formula I or a salt thereof. Particularly preferred is a method, wherein the plant's roots and shoots are protected, more preferably a method, wherein the plants shoots are protected form piercing and sucking insects, most preferably aa method, wherein the plants shoots are protected from aphids.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting.

The present invention also comprises seeds coated with or containing the active compound.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

In addition, the active compound may also be used for the treatment seeds from plants, which tolerate the action of herbicides or fungicides or insecticides owing to breeding, including genetic engineering methods.

For example, the active compound can be employed in treatment of seeds from plants, which are resistant to herbicides from the group consisting of the sulfonylureas, imidazolinones, glufosinate-ammonium or glyphosate-isopropylammonium and analogous active substances (see for example, EP-A-0242236, EP-A-242246) (WO 92/00377) (EP-A-0257993, U.S. Pat. No. 5,013,659) or in transgenic crop plants, for example cotton, with the capability of producing *Bacillus thuringiensis* toxins (Bt toxins) which make the plants resistant to certain pests (EP-A-0142924, EP-A-0193259), Furthermore, the active compound can be used also for the treatment of seeds from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the active compound is carried out by spraying or by dusting the seeds before sowing of the plants and before emergence of the plants.

Compositions which are especially useful for seed treatment are e.g.:
A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of compounds of formula I for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

Seed Treatment formulations may additionally also comprise binders and optionally colorants.

Binders can be added to improve the adhesion of the active materials on the seeds after treatment. Suitable binders are homo- and copolymers from alkylene oxides like ethylene oxide or propylene oxide, polyvinylacetate, polyvinylalcohols, polyvinylpyrrolidones, and copolymers thereof, ethylene-vinyl acetate copolymers, acrylic homo- and copolymers, polyethyleneamines, polyethyleneamides and polyethyleneimines, polysaccharides like celluloses, tylose and starch, polyolefin homo- and copolymers like olefin/maleic anhydride copolymers, polyurethanes, polyesters, polystyrene homo and copolymers Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of a gelling agent is carrageen (Satiagel®)

In the treatment of seed, the application rates of the compounds I are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed.

The invention therefore also relates to seed comprising a compound of the formula I, or an agriculturally useful salt of I, as defined herein. The amount of the compound I or the agriculturally useful salt thereof will in general vary from 0.1 g to 10 kg per 100 kg of seed, preferably from 1 g to 5 kg per 100 kg of seed, in particular from 1 g to 1000 g per 100 kg of seed. For specific crops such as lettuce the rate can be higher.

The present invention is now illustrated in further details by the following examples.

Some of the preferred compound examples are characterized by their physical data in the following table C.

Table C:

The products were characterized by coupled High Performance Liquid Chromatography/mass spectrometry (HPLC/MS), by NMR or by their melting points. Analytical HPLC column: RP-18 column Chromolith Speed ROD from Merck KgaA, Germany). Elution: acetonitrile+0.1% trifluoroacetic acid (TFA)/water+0.1% trifluoroacetic acid (TFA) in a ratio of from 5:95 to 95:5 in 5 minutes at 40° C.

Some compounds were characterized by $^1$H-NMR. The signals are characterized by chemical shift (ppm) vs. tetramethylsilane, by their multiplicity and by their integral (relative number of hydrogen atoms given). The following abbreviations are used to characterize the multiplicity of the signals: M=multiplett, q=quartett, t=triplett, d=doublet and s=singulett.

TABLE C

| Compound n° | Structure | Physical data: $T_{mp}$ (melting point) in [° C.] or HPLC-MS ($t_r$ retention time; M/Z) or $^1$H-NMR |
|---|---|---|
| C.1 | | $T_{mp}$ = 129-137 |
| C.2 | | $T_{mp}$ = 97-100 |
| C.3 | | $T_{mp}$ = 111-114 |
| C.4 | | $T_{mp}$ = 202-208 |
| C.5 | 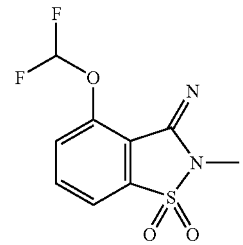 | $T_{mp}$ = 75-86 |
| C.6 | 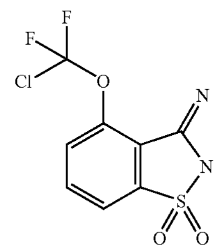 | $^1$H-NMR [DMSO-d6]: δ in ppm: 7.81(d, 1H), 8.01 (m, 2H), 9.26 (bs, 2H) |
| C.7 | 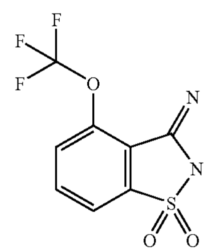 | $T_{mp}$ = 208-210 |
| C.8 | 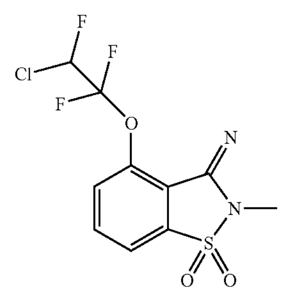 | $^1$H-NMR [CDCl3]: δ in ppm: 3.30 (s, 3H), 6.44 (dt, 1H), 7.21 (d, 1H), 7.84 (m, 2H) |
| C.9 | 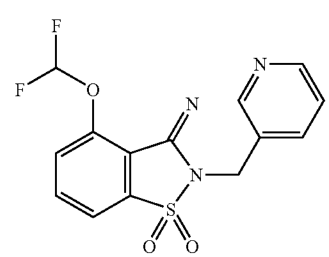 | $T_{mp}$ = 116-120 |
| C.10 | 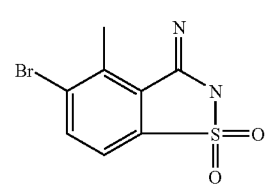 | oil |

TABLE C-continued

| Compound n° | Structure | Physical data: T_mp (melting point) in [° C.] or HPLC-MS (t_r retention time; M/Z) or ¹H-NMR |
|---|---|---|
| C.11 | (4-methyl, 5-cyano benzisothiazole-3-imine, N-ethyl, 1,1-dioxide) | T_mp = 148-156 |
| C.12 | (4-methyl, 5-cyano benzisothiazole-3-imine, N-cyclopropyl, 1,1-dioxide) | T_mp = 183-191 |
| C.13 | (4-trifluoromethyl benzisothiazole-3-imine, 1,1-dioxide) | T_mp = 217-222 |
| C.14 | (4-methyl benzisothiazole-3-imine, N-ethyl, 1,1-dioxide) | T_mp = 110-113 |
| C.15 | (4-methyl benzisothiazole-3-imine, N-(pyridin-3-ylmethyl), 1,1-dioxide) | T_mp = 203-206 |
| C.16 | (4-methyl, 3-butylamino benzisothiazole 1,1-dioxide) | HPLC-MS: t_r = 2.52 min; M/Z = 253 (M + 1) |
| C.17 | (4-methyl, 3-cyclopropylamino benzisothiazole 1,1-dioxide) | T_mp = 218-220 |
| C.18 | (4-methyl, 3-(2-methoxyethylamino) benzisothiazole 1,1-dioxide) | HPLC-MS: t_r = 1.93 min; M/Z = 255 (M + 1) |
| C.19 | (4-methyl, 3-(propargylamino) benzisothiazole 1,1-dioxide) | HPLC-MS: t_r = 1.92 min; M/Z = 235 (M + 1) |
| C.20 | (4-methoxy, 3-isopropylamino benzisothiazole 1,1-dioxide) | HPLC-MS: t_r = 2.12 min; M/Z = 255 (M + 1) |
| C.21 | (4-methoxy, 3-(N,N-dimethylhydrazino) benzisothiazole 1,1-dioxide) | HPLC-MS: t_r = 1.44 min; M/Z = 242 (M + 1) |
| C.22 | (4-methoxy, 3-cyclopropylamino benzisothiazole 1,1-dioxide) | HPLC-MS: t_r = 1.92 min; M/Z = 253 (M + 1) |
| C.23 | (4-methoxy, 3-propargylamino benzisothiazole 1,1-dioxide) | HPLC-MS: t_r = 1.86 min; M/Z = 251 (M + 1) |
| C.24 | (4-difluoromethoxy, 3-cyclopropylamino benzisothiazole 1,1-dioxide) | HPLC-MS: t_r = 2.25 min; M/Z = 289 (M + 1) |

TABLE C-continued

| Compound n° | Structure | Physical data: T$_{mp}$ (melting point) in [° C.] or HPLC-MS (t$_r$ retention time; M/Z) or $^1$H-NMR |
|---|---|---|
| C.25 | 4-(OCHF$_2$)-benzisothiazole-3-yl-NH-butyl, S,S-dioxide | T$_{mp}$ = 69-75 |
| C.26 | 4-(OCHF$_2$)-benzisothiazole-3-yl-NH-isopropyl, S,S-dioxide | HPLC-MS: t$_r$ = 2.65 min; M/Z = 291 (M + 1) |
| C.27 | 4-(OCHF$_2$)-benzisothiazole-3-yl-NH-CH$_2$-CN, S,S-dioxide | T$_{mp}$ = 219-224 |
| C.28 | 4-(OCHF$_2$)-benzisothiazole-3-yl-N(OCH$_3$), S,S-dioxide | T$_{mp}$ = 133-134 |
| C.29 | 4-(OCHF$_2$)-benzisothiazole-3-yl-NH-CH$_3$, S,S-dioxide | T$_{mp}$ = 139-141 |
| C.30 | 4-(OCHF$_2$)-benzisothiazole-3-yl-NH-ethyl, S,S-dioxide | T$_{mp}$ = 224-225 |
| C.31 | 4-(OCH$_3$)-benzisothiazole-3-yl-NH-ethyl | $^1$H-NMR [CDCl3]: δ in ppm: 1.33 (t, 3H), 3.57 (q, 2H), 4.01 (s, 3H), 6.30 (bs. 1H), 6.67 (d, 1H), 7.28 (d, 1H), 7.32 (t, 1H) |
| C.32 | 4-(OCH$_3$)-benzisothiazole-3-yl-NH-methyl | T$_{mp}$ = 65-67 |
| C.33 | 4-(OCHF$_2$)-benzisothiazole-3-yl-NH-ethyl, S-oxide | T$_{mp}$ = 64-70 |
| C.34 | 4-(OCH$_3$)-benzisothiazole-3-yl-NH-ethyl, S-oxide | HPLC-MS: t$_r$ = 1.75 min; M/Z = 225 (M + 1) |
| C.35 | 4-(OCH$_3$)-7-F-benzisothiazol-3(2H)-imine, 2-ethyl, S,S-dioxide | T$_{mp}$ = 136-140 |
| C.36 | 4-(OCH$_3$)-7-F-benzisothiazol-3(2H)-imine, 2-methyl, S,S-dioxide | $^1$H-NMR [d6-DMSO]: δ in ppm: 3.25 (s, 3H), 4.05 (s, 3H), 7.20 (dd, 1H), 7.35 (m, 1H), 8.95 (Br s, 1H). |

TABLE C-continued

| Compound n° | Structure | Physical data: T$_{mp}$ (melting point) in [° C.] or HPLC-MS (t$_r$ retention time; M/Z) or $^1$H-NMR |
|---|---|---|
| C.37 | (structure) | $^1$H-NMR [d6-DMSO]:δ in ppm: 3.98 (s, 3H), 7.45 (m, 1H), 7.67 (t, 1H), 8.05 (br s, 1H), 9.25 (br s, 1H). |
| C.38 | (structure) | T$_{mp}$ = 109-120 |
| C.39 | (structure) | T$_{mp}$ = 93-103 |
| C.40 | (structure) | T$_{mp}$ = 175-176 |
| C.41 | (structure) | HPLC-MS: t$_r$ = 2.10 min; M/Z = 259 (M + 1) |
| C.42 | (structure) | T$_{mp}$ = 182-187 |
| C.43 | (structure) | HPLC-MS: t$_r$ = 3.39 min; M/Z = 259 (M + 1) |
| C.44 | (structure) | T$_{mp}$ = 268-270 |
| C.45 | (structure) | T$_{mp}$ = 223-225 |
| C.46 | (structure) | T$_{mp}$ = 198-200 |
| C.47 | (structure) | $^1$H NMR (in CDCl$_3$): δ [ppm] = 2.36 (s, 1H), 4.60 (s, 2H), 6.42 (m, 1H), 7.71 (m, 1H), 7.82 (m, 2H), 9.09 (bs, 1H) |
| C.48 | (structure) | $^1$H NMR (in CDCl$_3$): δ [ppm] = 4.99 (s, 2H), 6.41 (m, 1H), 7.30 (m, 3H), 7.52 (m, 2H), 7.69 (m, 1H), 7.83 (m, 2H), 8.92 (bs, 1H) |

TABLE C-continued

| Compound n° | Structure | Physical data: T$_{mp}$ (melting point) in [° C.] or HPLC-MS (t$_r$ retention time; M/Z) or $^1$H-NMR |
|---|---|---|
| C.49 | [structure: 4-methoxy-5,7-difluoro-2-ethyl benzo[d]isothiazole-1,1-dioxide-3-imine] | HPLC-MS: t$_r$ = 1.77 min; M/Z = 277 (M + 1) |
| C.50 | [structure: 4-methoxy-5,7-difluoro benzo[d]isothiazole-1,1-dioxide-3-imine] | T$_{mp}$ = 220-224 |

SYNTHESIS EXAMPLES

S.1 2-Ethyl-4-methoxy-1,1-dioxo-1,2-dihydro-1λ*6*-benzo[d]isothiazol-3-ylideneamine (Compound example C.3)

1.50 g (6.24 mmol) 2-Cyano-N-ethyl-3-methoxy-benzenesulfonamide were added to a solution of 2.59 g (18.7 mmol) potassium carbonate in a mixture of 15 ml 1,4 dioxane and 6 ml of water. The solution was stirred for 24 h at room temperature. The solution was neutralized by addition of 10% HCl (pH=7). The solution was extracted twice with ethyl acetate. The organic layers were dried over Na$_2$SO$_4$ and concentrated. The crude product which still contained starting material was dissolved in a mixture of ethyl acetate and 10% HCl and vigorously shaken. The layers were separated and the aqueous layer was neutralized by addition of sodium bicarbonate. The aqueous layer was extracted twice with ethyl acetate. The organic layers were dried over Na$_2$SO$_4$ and concentrated to yield 830 mg (3.45 mmol) of the title compound having a melting point (T$_{mp}$) of 111-114° C.

S.2 4-Methyl-1,1-dioxo-1H-1λ*6*-benzo[d]isothiazol-3-yl)-prop-2-ynyl-amine (Compound example C.19):

Step 1: Synthesis of 2-Cyano-N-diethoxymethylene-3-methyl-benzenesulfonamide 3.60 g (18.4 mmol) 2-cyano-3-methyl-benzenesulfonamide and 5.29 g tetraethoxymethane (27.5 mmol) were heated to 160° C. slowly with stirring under removal of ethanol from the mixture. The mixture was cooled to room temperature. The residue was digerated with petrol ether, filtered and dried to afford 4.91 g (90% of theory) 2-Cyano-N-diethoxymethylene-3-methyl-benzene-sulfon-amide.

Step 2: Synthesis of 4-Methyl-1,1-dioxo-1H-1λ*6*-benzo[d]isothiazol-3-yl)-prop-2-ynyl-amine (C.19)

500 mg (1.69 mmol) 2-Cyano-N-diethoxymethylene-3-methyl-benzenesulfon-amide and 930 mg (16.9 mmol) propargyl amine were heated to 70° C. for 4 h. All volatiles were removed in vacuum. The residue was digerated with dichloromethane to obtain 246 mg (1.05 mmol; 62% of theory) of the title compound (C.19)

S.3. (4-Difluoromethoxy-1,1-dioxo-1H-1λ*6*-benzo[d]isothiazol-3-yl)-isopropylamine (Compound example C.26)

400 mg (1.5 mmol) 3-Chloro-4-difluoromethoxy-benzo[d]isothiazole 1,1-dioxide were dissolved in 5 ml dry THF and cooled to 0° C. 883 mg (15.0 mmol) isopropylamine was dissolved in 5 ml dry THF and added slowly. Stirring was continued for 1 h at this temperature and for 14 h at room temperature. The mixture was concentrated in vacuum. The residue was purified on silica (eluent: cyclohexane/ethyl acetate 4:1) to afford 140 mg (0.48 mmol; 32% of theory) of the title compound (C.26).

S.4 (4-Methoxy-benzo[d]isothiazol-3-yl)-methyl-amine (Compound example C.32)

Step 1: Synthesis of sodium 2-cyano-3-methoxy-benzenethiolate 15.5 g (93.8 mmol) 4-Methoxy-benzo[d]isothiazole were dissolved in 200 ml ethylene glycol dimethyl ether at room temperature. 10.45 g (188 mmol) sodium methoxide were added. The mixture was heated to 80° C. for 8 h and stirring was continued at room temperature for 16 h. The mixture was divided and one quarter of the mixture was used in the subsequent synthesis without further purification.

Step 2: Synthesis of (4-Methoxy-benzo[d]isothiazol-3-yl)-methyl-amine (C.32)

To the reaction mixture of the precedent reaction were added 55 g (704 mmol) methyl amine in THF. The mixture was cooled to 0° C. 34.9 g (23.5 mmol) of a 5% NaOCl—solution were added slowly. The mixture was stirred overnight under warm-up to room temperature. The reaction mixture was poured into water. The mixture was extracted with ethyl acetate. The organic layer was dried over Na$_2$SO$_4$ and concentrated. The crude product was purified on silica (eluent cyclohexan/ethyl acetate) to yield 3.04 g (15.7 mmol) of the title product as a brownish oil.

S.5 Ethyl-(4-methoxy-1-oxo-1H-1λ*4*-benzo[d]isothiazol-3-yl)-amine (Compound example C.34)

90 mg (0.43 mmol) Ethyl-(4-Methoxy-benzo[d]isothiazol-3-yl)-amine, prepared in analogy to compound example 32, was dissolved in 10 ml dichloromethane. The solution was cooled to 0 C and 100 mg of a 70% m-chlor-perbenzoic acid was added portion wise. The cooling bath was removed and stirring was continued for 30 min at room temperature. The solution was poured into Na$_2$CO$_3$-solution. The layers were separated and the organic layer was washed with Na$_2$CO$_3$-solution and water. The organic layer was dried over NaSO$_4$ and concentrated. The crude product was purified by reverse-phase HPLC (eluent acetonitrile/water) to yield 40 mg (0.18 mmol) of the title product.

B. Biological Examples of Action Against Pests

The active compounds were formulated in a mixture of 50 vol.-% acetone:50 vol.-% water. A nonionic surfactant (Kinetic®) was included in the solution at a volume of 0.01% v/v.

In the following tests, the formulated solutions of the active compounds were diluted to an active ingredient concentration of 300 ppm and the diluted solutions were applied in the below mentioned tests.

The action of the compounds of the formula I against pests was demonstrated by the following experiments:

B.1 Cotton Aphid (*Aphis gossypii*), Mixed Life Stages

Cotton plants at the cotyledon stage were infested prior to treatment by placing a heavily infested leaf from the main aphid colony on top of each cotyledon. The aphids were allowed to transfer overnight and the host leaf was removed. The infested cotyledons were then dipped and agitated in the test solution for 3 seconds and allowed to dry in a fume hood. Test plants were maintained under fluorescent lighting in a 24-hr photoperiod at 25° C. and 20-40% relative humidity. Aphid mortality on the treated plants, relative to mortality on untreated check plants, was determined after 5 days.

In this test compound examples 1-9, 11, 13, 14, 17, 19-22, 26-46, 49 and 50 provided at 300 ppm at least 86% mortality of cotton aphid (*Aphis gossypii*, mixed life stages) in comparison with untreated controls.

B.2 Green Peach Aphid (*Myzus persicae*), Mixed Life Stages

Bell pepper plants at the first true-leaf stage were infested prior to treatment by placing heavily infested leaves from the main aphid colony on top of the treatment plants. The aphids were allowed to transfer overnight to accomplish an infestation of 30-40 aphids per plant and the host leaves were removed. The infested leaves of the test plants were then dipped and agitated in the test solution for 3 seconds and allowed to dry in a fume hood. Test plants were maintained under fluorescent lighting in a 24-hr photoperiod at 25° C. and 20-40% relative humidity. Aphid mortality on the treated plants, relative to mortality on untreated check plants, was determined after 5 days.

In this test compound examples 1-5, 9, 14, 19, 20, 24, 26-46, 49 and 50 provided at 300 ppm at least 86% mortality of green peach aphid in comparison with untreated controls.

B.3 Bean Aphid (*Aphis fabae*)

Nasturtium plants grown in Metro mix in the 1$^{st}$ leaf-pair stage (variety 'Mixed Jewel') were infested with approximately 2-30 laboratory-reared aphids by placing infested cut plants on top of the test plants. The cut plants were removed after 24 hr. Each plant was dipped into the test solution to provide complete coverage of the foliage, stem, protruding seed surface and surrounding cube surface and allowed to dry in the fume hood. The treated plants were kept at about 25° C. with continuous fluorescent light. Aphid mortality is determined after 3 days.

In this test compound examples 2-6, 9, 13, 14, 16, 17 and 24 provided at 300 ppm provided at least 86% mortality of bean aphid in comparison with untreated controls.

The invention claimed is:
1. 3-amino-1,2-benzisothiazole compounds of formula I

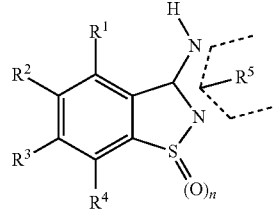

(I)

wherein
n is 0;
R$^1$ is selected from C$_1$-C$_6$-alkyl, C$_1$-C$_6$-haloalkyl, C$_2$-C$_6$-alkenyl, C$_2$-C$_6$-haloalkenyl, C$_2$-C$_6$-alkynyl, C$_2$-C$_6$-haloalkynyl, C$_3$-C$_8$-cycloalkyl, C$_3$-C$_6$-halocycloalkyl, C$_1$-C$_6$-alkoxy, C$_1$-C$_6$-haloalkoxy, wherein the mentioned radicals may be unsubstituted or may carry 1, 2 or 3 radicals, selected from the group consisting of cyano, nitro, amino, C$_1$-C$_4$-alkoxy, C$_1$-C$_4$alkylthio, C$_1$-C$_4$-alkylsulfinyl, C$_1$-C$_4$-alkylsulfonyl, C$_1$-C$_4$-haloalkoxy, C$_1$-C$_4$-haloalkylthio, (C$_1$-C$_4$-alkoxy)carbonyl, (C$_1$-C$_4$-alkyl)amino, di(C$_1$-C$_4$-alkyl)amino, aminocarbonyl, (C$_1$-C$_4$-alkyl)aminocarbonyl, di(C$_1$-C$_4$-alkyl)aminocarbonyl, C$_3$-C$_8$-cycloalkyl and phenyl, it being possible for phenyl to be unsubstituted, partially or fully halogenated and/or to carry 1, 2 or 3 substituents, independently of one another selected from the group consisting of CN, C$_1$-C$_4$-alkyl, C$_1$-C$_4$-haloalkyl, C$_1$-C$_4$-alkoxy and C$_1$-C$_4$-haloalkoxy and
R$^2$, R$^3$ and R$^4$ are independently of one another selected from the group consisting of hydrogen, halogen, cyano, azido, nitro, C$_1$-C$_6$-alkyl, C$_3$-C$_8$-cycloalkyl, C$_1$-C$_4$-haloalkyl, C$_1$-C$_4$-alkoxy, C$_1$-C$_4$-alkylthio, C$_1$-C$_4$-alkylsulfinyl, C$_1$-C$_4$-alkylsulfonyl, C$_1$-C$_4$-haloalkoxy, C$_1$-C$_4$-haloalkylthio, C$_2$-C$_6$-alkenyl, C$_2$-C$_6$-alkynyl, (C$_1$-C$_4$-alkoxy)carbonyl, amino, (C$_1$-C$_4$-alkyl)amino, di(C$_1$-C$_4$-alkyl)amino, aminocarbonyl, (C$_1$-C$_4$alkyl)aminocarbonyl, di(C$_1$-C$_4$-alkyl)aminocarbonyl, sulfonyl, sulfonylamino, sulfenylamino, sulfanylamino and C(=O)—R$^{2a}$ or C(=O)—R$^{3a}$ or C(=O)—R$^{4a}$, and wherein, R$^{2a}$ or R$^{3a}$ or R$^{4a}$ are selected from the group consisting of hydrogen, hydroxy, C$_1$-C$_6$-alkoxy, amino, C$_1$-C$_6$-alkyl, aryl, aryl-C$_1$-C$_6$-alkyl, (C$_1$-C$_6$-alkyl)-amino, di-(C$_1$-C$_6$-alkyl)-amino, 3- to 7-membered heteroaryl or heteroaryl-C$_1$-C$_4$-alkyl, wherein the heteroaryl ring contains as ring members 1, 2 or 3 heteroatoms, selected from the group consisting of nitrogen, oxygen, sulfur, a group SO, SO$_2$ or NR$^{2b}$ or NR$^{3b}$ or NR$^{4b}$, and wherein R$^{2b}$ or R$^{3b}$ or R$^{4b}$ are hydrogen, C$_1$-C$_6$-alkyl or (C$_1$-C$_6$-alkyl)-carbonyl;
R$^5$ is selected from the group consisting of OR$^{5a}$, C$_1$-C$_{10}$-alkyl, C$_2$-C$_{10}$-alkenyl, C$_2$-C$_{10}$-alkynyl, C$_3$-C$_{10}$-cycloalkyl, aryl-C$_1$-C$_4$-alkyl, heteroaryl-C$_1$-C$_4$-alkyl, heterocyclyl-C$_1$-C$_4$-alkyl, wherein these radicals may be unsubstituted, partially or fully halogenated and/or may carry 1-4 radicals selected from the group consisting of C$_1$-C$_{10}$-alkoxy, C$_1$-C$_{10}$-alkylthio, C$_1$-C$_{10}$-alkylsulfinyl, C$_1$-C$_{10}$-alkylsulfonyl, C$_1$-C$_{10}$-haloalkoxy, C$_1$-C$_{10}$-haloalkylthio, (C$_1$-C$_{10}$-alkoxy)carbonyl, cyano, nitro, amino, (C$_1$-C$_{10}$-alkyl)amino, di-(C$_1$-C$_{10}$-alkyl)amino, C$_3$-C$_{10}$-cycloalkyl and phenyl, it being possible for phenyl to be unsubstituted, partially or fully halogenated and/or to carry 1-3 substituents selected from the group consisting of CN, $C_1$-$C_6$-alkyl, $C_1$-$C_6$-haloalkyl, $C_1$-$C_6$-alkoxy, $C_1$-$C_6$-haloalkoxy, and wherein $R^{5a}$ is selected from hydrogen, $C_1$-$C_{10}$-alkyl, $C_1$-$C_{10}$-acyl, $C_3$-$C_{10}$-cycloalkyl, $C_2$-$C_{10}$-alkenyl, $C_2$-$C_{10}$-alkynyl, aryl, aryl-$C_1$-$C_4$-alkyl, heteroaryl and heteroaryl-$C_1$-$C_4$-alkyl, heterocyclyl or heterocyclyl-$C_1$-$C_4$-alkyl and wherein all radicals may be unsubstituted, partially or fully halogenated and/or may carry 1, 2 or 3 radicals, selected from the group consisting of cyano, nitro, amino, $C_1$-$C_4$-alkoxy, $C_1$-$C_4$-alkylthio, $C_1$-$C_4$-alkylsulfinyl, $C_1$-$C_4$-alkylsulfonyl, $C_1$-$C_4$haloalkoxy, $C_1$-$C_4$-haloalkylthio, ($C_1$-$C_4$-alkoxy)carbonyl, ($C_1$-$C_4$-alkyl)amino, di($C_1$-$C_4$-alkyl)amino and $C_3$-$C_8$-cycloalkyl;

or the enantiomers, distereomers or salts thereof, with the proviso that the 3-amino-1,2-benzisothiazole compound of formula I is not 4-Methoxy-N-(2-methyl-2-phenylpropyl)benzo[d]isothiazol-3-amine, 4-Methoxy-N-(2-methyl-2-(6-methylpyridin-2-yl)propyl)benzo[d]isothiazol-3-amine or not $N^1$-(4-Methylbenzo[d]isothiazol-3-yl)propane-1,3-diamine.

2. 3-amino-1,2 benzisothiazole compounds of formula I according to claim 1, wherein $R^1$ is selected from $C_1$-$C_6$-alkoxy or $C_1$-$C_6$-haloalkoxy.

3. 3-amino-1,2 benzisothiazole compounds of formula I according to claim 1, wherein $R^1$ is selected from $C_1$-$C_6$-fluoroalkoxy or $C_1$-$C_6$-chloroalkoxy.

4. 3-amino-1,2 benzisothiazole compounds of formula I according to claim 1, wherein $R^2$, $R^3$ and $R^4$ are independently of one another selected from the group consisting of hydrogen, F, Cl, Br or J.

5. 3-amino-1,2 benzisothiazole compounds of formula I according to claim 1, wherein $R^2$, $R^3$ and $R^4$ are independently of one another hydrogen or fluoro.

6. 3-amino-1,2 benzisothiazole compounds of formula I according to claim 1, wherein $R^2$, $R^3$ and $R^4$ are hydrogen.

7. 3-amino-1,2 benzisothiazole compounds of formula I according to claim 1, wherein:

$R^5$ is selected from $C_1$-$C_6$-alkyl, which may be unsubstituted, partially or fully halogenated and/or may carry 1-4 radicals selected from the group consisting of $C_1$-$C_{10}$-alkoxy, $C_1$-$C_{10}$-alkylthio, $C_1$-$C_{10}$-alkylsulfinyl, $C_1$-$C_{10}$-alkylsulfonyl, $C_1$-$C_{10}$-haloalkoxy, $C_1$-$C_{10}$-haloalkylthio, ($C_1$-$C_{10}$-alkoxy)carbonyl, cyano, nitro, amino, ($C_1$-$C_{10}$-alkyl)amino, di-($C_1$-$C_{10}$-alkyl)amino, $C_3$-$C_{10}$-cycloalkyl and phenyl, it being possible for phenyl to be unsubstituted, partially or fully halogenated and/or to carry 1-3 substituents selected from the group consisting of CN, $C_1$-$C_6$-alkyl, $C_1$-$C_6$-haloalkyl, $C_1$-$C_6$-alkoxy, $C_1$-$C_6$-haloalkoxy.

8. 3-amino-1,2 benzisothiazole compounds of formula I according to claim 1, wherein:

$R^1$ is selected from $C_1$-$C_6$-alkoxy or $C_1$-$C_6$-haloalkoxy and $R^2$, $R^3$ and $R^4$ are independently of one another selected from the group consisting of hydrogen, F, Cl, Br or J.

9. 3-amino-1,2 benzisothiazole compounds of formula I according to claim 1, wherein:

$R^1$ is selected from $C_1$-$C_6$-alkoxy or $C_1$-$C_6$-haloalkoxy and $R^2$, $R^3$ and $R^4$ are hydrogen.

10. 3-amino-1,2 benzisothiazole compounds of formula I according to claim 1, wherein:

$R^1$ is selected from $C_1$-$C_6$-alkoxy or $C_1$-$C_6$-haloalkoxy;

$R^2$, $R^3$ and $R^4$ are independently of one another selected from the group consisting of hydrogen, F, Cl, Br or J; and $R^5$ is selected from $C_1$-$C_6$-alkyl, which may be unsubstituted, partially or fully halogenated and/or may carry 1-4 radicals selected from the group consisting of $C_1$-$C_{10}$-alkoxy, $C_1$-$C_{10}$-alkylthio, $C_1$-$C_{10}$-alkylsulfinyl, $C_1$-$C_{10}$-alkylsulfonyl, $C_1$-$C_{10}$-haloalkoxy, $C_1$-$C_{10}$-haloalkylthio, ($C_1$-$C_{10}$-alkoxy)carbonyl, cyano, nitro, amino, ($C_1$-$C_{10}$-alkyl)amino, di-($C_1$-$C_{10}$-alkyl)amino, $C_3$-$C_{10}$-cycloalkyl and phenyl, it being possible for phenyl to be unsubstituted, partially or fully halogenated and/or to carry 1-3 substituents selected from the group consisting of CN, $C_1$-$C_6$-alkyl, $C_1$-$C_6$-haloalkyl, $C_1$-$C_6$-alkoxy, $C_1$-$C_6$-haloalkoxy.

11. A composition comprising at least one 3-amino-1,2-benzisothiazole compound of the formula I according to claim 1, or the enantiomer, diastereomer or salt thereof and at least one inert liquid and/or solid carrier.

12. A method for combating or controlling animal pests comprising contacting the animal pests or their food supply, habitat or breeding grounds with a pesticidally effective amount of at least one 3-amino-1,2-benzisothiazole compound of the formula I according to claim 1, or the enantiomers, diastereomers or salts thereof.

13. A method for protecting growing plants from attack or infestation by animal pests comprising contacting a plant, or soil or water in which the plant is growing, with a pesticidally effective amount of at least one 3-amino-1,2-benzisothiazole compound of the formula I according to claim 1, or the enantiomers, diastereomers or salts thereof.

14. A method for the protection of seeds from soil insects and of the seedlings' roots and shoots from soil and foliar insects comprising contacting the seeds before sowing and/or after pregermination with at least one 3-amino-1,2-benzisothiazole compound of the formula I according to claim 1, or the enantiomers, diastereomers or salts thereof.

15. Seed comprising an 3-amino-1,2-benzisothiazole compound of the formula I as defined in claim 1, or the enantiomer, diastereomer or agriculturally acceptable salt thereof, in an amount of from 0.1 g to 10 kg per 100 kg of seed.

16. A composition comprising at least one 3-amino-1,2-benzisothiazole compound of the formula I according to claim 8, or the enantiomer, diastereomer or salt thereof and at least one inert liquid and/or solid carrier.

17. A method for combating or controlling animal pests comprising contacting the animal pests or their food supply, habitat or breeding grounds with a pesticidally effective amount of at least one 3-amino-1,2-benzisothiazole compound of the formula I according to claim 8, or the enantiomers, diastereomers or salts thereof.

18. A method for protecting growing plants from attack or infestation by animal pests comprising contacting a plant, or soil or water in which the plant is growing, with a pesticidally effective amount of at least one 3-amino-1,2-benzisothiazole compound of the formula I according to claim 8, or the enantiomers, diastereomers or salts thereof.

19. A method for the protection of seeds from soil insects and of the seedlings' roots and shoots from soil and foliar insects comprising contacting the seeds before sowing and/or after pregermination with at least one 3-amino-1,2-benzisothiazole compound of the formula I according to claim 8, or the enantiomers, diastereomers or salts thereof.

20. Seed comprising an 3-amino-1,2-benzisothiazole compound of the formula I as defined in claim 8, or the enantiomer, diastereomer or agriculturally acceptable salt thereof, in an amount of from 0.1 g to 10 kg per 100 kg of seed.

\* \* \* \* \*